(12) United States Patent
Jandacek et al.

(10) Patent No.: US 8,372,430 B2
(45) Date of Patent: Feb. 12, 2013

(54) COMPOSITIONS, METHODS, AND KITS USEFUL FOR THE ALLEVIATION OF GASTROINTESTINAL EFFECTS

(75) Inventors: Ronald James Jandacek, Cincinnati, OH (US); William Randall Francis, Cincinnati, OH (US); Gary Robert Kelm, Cincinnati, OH (US); Bryn Hird, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 954 days.

(21) Appl. No.: 10/699,351

(22) Filed: Oct. 31, 2003

(65) Prior Publication Data
US 2004/0126424 A1 Jul. 1, 2004

Related U.S. Application Data

(60) Provisional application No. 60/434,156, filed on Dec. 17, 2002.

(51) Int. Cl.
*A61K 9/20* (2006.01)
(52) U.S. Cl. ....................................................... 424/465
(58) Field of Classification Search .................. 424/465
See application file for complete search history.

(56) References Cited

U.S. PATENT DOCUMENTS

| | | |
|---|---|---|
| 3,923,976 A | 12/1975 | Regife Vega et al. |
| 3,980,968 A | 9/1976 | Ma |
| 4,005,196 A | 1/1977 | Jandacek et al. |
| 4,211,765 A | 7/1980 | Johnson et al. |
| 4,223,023 A | 9/1980 | Furda |
| 4,241,054 A | 12/1980 | Volpenhein et al. |
| 4,340,699 A | 7/1982 | Grouiller |
| 4,432,968 A | 2/1984 | Page et al. |
| 4,598,089 A | 7/1986 | Hadvary et al. |
| 5,149,720 A | 9/1992 | DesMarais et al. |
| 5,189,070 A | 2/1993 | Brownscombe et al. |
| 5,260,345 A | 11/1993 | DesMarais et al. |
| 5,268,224 A | 12/1993 | DesMarais et al. |
| 5,290,820 A | 3/1994 | Brownscombe et al. |
| 5,387,207 A | 2/1995 | Dyer et al. |
| 5,447,953 A | 9/1995 | Isler et al. |
| 5,453,282 A | 9/1995 | Kanauchi et al. |
| 5,563,179 A | 10/1996 | Stone et al. |
| 5,650,222 A | 7/1997 | DesMarais et al. |
| 5,741,518 A | 4/1998 | Ribier et al. |
| 5,750,585 A * | 5/1998 | Park et al. ..................... 521/143 |
| 5,817,704 A | 10/1998 | Shiveley et al. |
| 5,827,909 A | 10/1998 | DesMarais |
| 6,030,953 A | 2/2000 | Bailly et al. |
| 6,207,724 B1 | 3/2001 | Hird et al. |
| 6,358,522 B1 * | 3/2002 | Hug et al. ..................... 424/441 |
| 6,624,161 B2 | 9/2003 | Hodson et al. |
| 6,703,369 B1 * | 3/2004 | de Smidt et al. ................ 514/23 |
| 6,730,319 B2 | 5/2004 | Maeder et al. |

FOREIGN PATENT DOCUMENTS

| | | |
|---|---|---|
| WO | WO 98/22072 A1 | 5/1998 |
| WO | WO 99/34787 A2 | 7/1999 |
| WO | WO 00/09122 A1 | 2/2000 |
| WO | WO 00/09122 A1 | 2/2000 |
| WO | WO 00/40247 A1 | 7/2000 |
| WO | WO 00/40569 A1 | 7/2000 |
| WO | WO 01/19340 A1 | 3/2001 |
| WO | WO 01/19378 A2 | 3/2001 |
| WO | WO 01/53278 A1 | 7/2001 |
| WO | WO 02/074343 A2 | 9/2002 |
| WO | WO 02/098412 A1 | 12/2002 |
| WO | WO 02/098413 A2 | 12/2002 |

OTHER PUBLICATIONS

McDonald et al., British J. of Nutrition 86 487-489 (2001).*
Behenic acid properties 2000 p. 1.*
Yamamoto et al., "Anti-obesity effects of lipase inhibitor CT-II, an extract from edible herbs, Nomame Herba, on rats fed a high-fat diet", International journal of Obesity (2000) 24, 758-764.
Chiou et al., "Synthetic Routes and Lipase-Inhibiting Activity of Long-Chain O -Keto Amides" Lipids, vol. 36, No. 5 (2001).
Han et al., "Anti-obesity effects in rodents of dietary teasaponin, a lipae inhibitor", International Journal of Obesity (2001) 25, 1459-1464.
Cavalier et al., Inhibition of human gastric and pancreatic lipases by chiral alkylphosphonates. A kinetic study with 1, 2-didecanoyl-sn-glycerol monolayer, Chemistry and Physics of Lipids 100 (1999) 3 31.
Tomoda et al., "Differential Inhibition of HMG-CoA Synthase and Pancreatic Lipase by the Specific Chiral Isomers of B-Lactone Du-6622", Biochemical and Biophysical Research Communications 265, 536-540 (1999).
Miller et al., Disposition of Ingested Olestra in the Fischer 344 Rat(1), Fundamental and Applied Toxicology 24, 229-237 (1995).

(Continued)

*Primary Examiner* — Shirley V Gembeh
(74) *Attorney, Agent, or Firm* — Alexandra S. Anoff

(57) ABSTRACT

Disclosed are compositions, methods, and kits for treating conditions including; ameliorating side effects associated with compounds such as lipase inhibitors; gastrointestinal distress; fecal urgency; obesity; hyperlipidemia; diarrhea; reducing levels of toxic substances; reducing blood cholesterol levels; inducing satiety; effecting weight loss; effecting weight control; and treating, delaying onset and/or preventing Type II diabetes. One embodiment includes compositions for administration to an animal for stiffening lipophilic substances in the gastrointestinal tract. Such stiffening agents have a complete melting point of about 33° C. or greater. Kits comprising the composition are also included. Methods of stiffening lipophilic substances present in the gastrointestinal tract of an animal are also provided. The methods comprise administering a composition comprising a safe and effective amount of a stiffening agent to an animal. The methods also comprise administering a composition comprising a safe and effective amount of a stiffening agent and a safe and effective amount of a lipase inhibitor to an animal.

9 Claims, No Drawings

OTHER PUBLICATIONS

Flamm et al., "Inulin and Oligofructose as Dietary Fiber: A Review of the Evidence", Critical Reviews in Food Science and Nutrition, 41(5):353-362 (2001).

Comai et al., Antiobesity activity of pluronic L-101, International Journal of Obesity (1980) 4, 33-42.

* cited by examiner

COMPOSITIONS, METHODS, AND KITS USEFUL FOR THE ALLEVIATION OF GASTROINTESTINAL EFFECTS

CROSS REFERENCE TO RELATED APPLICATIONS

This application claims priority under Title 35, United States Code §119(e) from Provisional Application Ser. No. 60/434,156, filed Dec. 17, 2002.

FIELD OF THE INVENTION

The present invention relates to compositions comprising a stiffening agent, wherein the compositions are useful for stiffening unabsorbed dietary fat and oil present in the gastrointestinal tract, thereby reducing gastrointestinal side effects and separation of these substances from fecal matter. The invention further relates to compositions that are useful for a variety of treatments, for example weight control, wherein the side effects associated with lipase inhibitors are ameliorated. This invention additionally relates to kits comprising the compositions and methods of using the compositions and kits.

BACKGROUND OF THE INVENTION

A significant portion of the American population is considered to be obese, with an even larger portion of this population considered to be overweight. Obesity is also considered to be a growing problem in other industrialized countries and in developing countries where large numbers of people have become accustomed to Western-influenced high-caloric diets. It has been estimated that obesity contributes to 50% of chronic diseases in Western societies and is responsible for approximately 70% of preventable deaths in the United States. Health care costs associated with obesity are substantial. As a result, the development of compositions to effect weight loss is the subject of significant commercial interest.

Approaches to weight control include appetite suppressants, reduced-caloric diets, exercise regimens, inhibition of dietary nutrient absorption (for example, lipids), surgical procedures and the like. A variety of compositions for weight control have been developed. Desired characteristics for such products include the lack of undesirable side effects, high efficacy, convenient dosage regimens, and low cost. Drugs developed to treat obesity may have undesirable side effects, may be available only under medical supervision, and may be relatively expensive. Other products such as those with high fiber content may require inconveniently large doses to be effective.

One method of inhibiting the absorption of dietary lipids is by inhibiting digestion and/or metabolism of these lipids via administration of a suitable non-absorbable material to bind or sequester the lipids. For example, U.S. Pat. No. 4,223,023, Furda, issued Sep. 16, 1980, describes the ingestion of chitosan to bind fatty acids and prevent their utilization. Similarly, U.S. Pat. No. 5,453,282, Kanauchi et al., issued Sep. 26, 1995, describes dietary lipid absorption-inhibiting agents comprising a mixture of chitosan and ascorbic acid or a salt thereof. However, the efficacy of chitosan in increasing fat excretion is relatively low, requiring impracticably large doses to be effective as a dietary weight-control supplement. (See, for example, Lengsfeld et al., Obesity Research, Vol. 7, Suppl. 1, November 1999). Certain fat-imbibing polymer particles are described in U.S. Pat. No. 4,432,968 Page et al., issued Feb. 21, 1984. Fat-binding polymers are also described in WO 99/34787, Mandeville et al., published Jul. 15, 1999. Similarly, U.S. Pat. No. 3,980,968, Ingleman et al., issued Sep. 14, 1976, describes certain solid network (i.e., crosslinked) polymers containing amino groups for binding bile acids. Solid crosslinked polyurethane polymers which form a gel in the presence of water and which are capable of binding cholesterol and lipids have been described as in U.S. Pat. No. 4,340,699, Grouiller, issued Jul. 20, 1982.

Another approach to inhibiting the digestion and/or metabolism of dietary lipids is to utilize compounds that inhibit the activity of certain enzymes necessary for digestion of lipids. Polymers which inhibit the action of pancreatic lipase are described in U.S. Pat. No. 3,923,976, Fields and Johnson, issued Dec. 2, 1975 and U.S. Pat. No. 4,211,765, Johnson and Fields, issued Jul. 8, 1980. However, the efficacy of these materials in inhibiting lipid digestion is also low, as measured by fat excretion.

Other lipase inhibitors can reduce the digestion of fat and oil, thereby causing the elimination of unabsorbed fat and oil through the feces. Examples of lipase inhibitors include tetrahydrolipstatin (orlistat; XENICAL®) described in U.S. Pat. No. 4,598,089, Hadvary et al., issued Jul. 1, 1986; lipase inhibitors including 2-amino-4H-3,1-benzoxazin-4-one and its derivatives described in WO 0040247 published Jul. 13, 2000; 2-oxy-4H-3,1-benzoxazin-4-ones and its derivatives described in WO 0040569, published Jul. 13, 2000; 2-thio-4H-3,1-benzoxazin-4-one and its derivatives described in WO 0153278, published Jul. 26, 2001; teasaponin described in Han et al., Int. J. Obes. Relat. Metab. Disord., Vol. 25, pp. 1459-1464, 2001; long-chain alpha-keto amides described in Chiou et al., Lipids, Vol. 36, pp. 535-542, 2001; extract of Nomame Herba described in Yamamoto et al., Int. J. Obes. Relat. Metab. Disord., Vol. 24, pp. 758-764, 2000; chiral alkylphosphonates described in Cavalier et al., Chem. Phys. Lipids, Vol. 100, pp. 3-31, 1999; chiral isomers of beta-lactone described in Tomoda et al., Biochem. Biophys. Res. Commun., Vol. 265, pp. 536-540, 1999; and Pluronic L-101 described in Comai et al., Int. J. Obes., Vol. 4, pp. 33-42, 1980.

However, anal leakage of undigested oil is an adverse side effect often observed in subjects treated with sufficiently large doses of lipase inhibitors to be effective in the treatment of obesity. Several approaches have been described to ameliorate this side effect. Combining a lipase inhibitor with substantial amounts of water-insoluble crude fiber to increase the inhibition of fat absorption is described in U.S. Pat. No. 5,447,953, Isler et al., issued Sep. 5, 1995. Combining a lipase inhibitor with certain poorly digestible, poorly fermentable hydrophilic, hydrocolloidal food grade thickeners, or emulsifiers to reduce anal leakage is described in WO 00/09122, Hug et al., published Feb. 24, 2000. Similarly, combining a lipase inhibitor with chitosan or a derivative or salt thereof to reduce anal leakage is described in U.S. Pat. No. 6,030,953, Bailly et al., issued Feb. 29, 2000. However, at convenient dosage levels, the efficacy of such materials in eliminating anal leakage is relatively low, as evidenced by significant levels of oily fur greasing in rodents.

As described above, the use of effective doses of agents that inhibit certain enzymes necessary for the digestion and absorption of fats and oils can lead to significant undesirable symptoms. Known materials that sequester or bind dietary lipids typically have low efficacy, requiring inconveniently large doses to be effective in the prevention or treatment of obesity, or in ameliorating the side effects associated with certain drugs, laxatives and fat-substitutes.

Accordingly, it would be desirable to develop a composition useful for treatments such as weight control that: (1) is suitable for ingestion; (2) has minimal undesirable side effects; (3) has high efficacy; (4) has convenient dosage regimens; and (5) is broadly applicable to various lipids, lipid substitutes, and other lipophilic substances.

SUMMARY OF THE INVENTION

The present invention relates to compositions suitable for a variety of treatments, including ameliorating the undesirable side effects associated with compounds such as lipase inhibitors (e.g., anal leakage of undigested fat or oil). In particular, one embodiment of the present invention relates to compositions that are suitable for administration to an animal for the purpose of stiffening one or more lipophilic substances present in the gastrointestinal tract of the animal. Another embodiment of the present invention relates to compositions comprising:
  (a) a stiffening agent as described herein, wherein the stiffening agent has a complete melting point of about 33° C. or greater; and
  (b) a lipase inhibitor; wherein the ratio of the stiffening agent to the lipase inhibitor, by weight, is at least about 1:1 (for example, from about 1:1 to about 50:1).

In yet another embodiment herein, methods of stiffening lipophilic substances present in the gastrointestinal tract of an animal are provided, wherein the methods comprise administering a composition comprising a safe and effective amount of a stiffening agent to the animal, wherein the stiffening agent is described herein and has a complete melting point of about 33° C. or greater. The methods herein also include those selected from treating gastrointestinal distress, treating fecal urgency, treating obesity, treating hyperlipidemia, treating diarrhea, inhibiting anal leakage, reducing levels of toxic substances, reducing blood cholesterol levels, inducing satiety, effecting weight loss, effecting weight control, treating Type II Diabetes, delaying onset of Type II Diabetes, preventing Type II Diabetes, and combinations thereof, the methods comprising administering a composition comprising a safe and effective amount of the stiffening agent to the animal, as well as a safe and effective amount of a lipase inhibitor.

Various kits are also provided herein, including kits comprising:
  (a) a first composition comprising a stiffening agent as described herein, wherein the stiffening agent has a complete melting point of about 33° C. or greater; and
  (b) a second composition comprising a lipase inhibitor.
Other kits include those comprising:
  (a) a composition comprising a stiffening agent as described herein, wherein the stiffening agent has a complete melting point of about 33° C. or greater; and
  (b) a lipase inhibitor; and
  (c) information associated with the composition that use of the composition will provide one or more benefits selected from the group consisting of treatment of gastrointestinal distress, treatment of fecal urgency, treatment of obesity, weight loss, weight control, treatment of hyperlipidemia, treatment of diarrhea, inhibition of anal leakage, reduction of levels of toxic substances, treatment of Type II Diabetes, delay of onset of Type II Diabetes, prevention of Type II Diabetes, and combinations thereof.

These and other embodiments of the present invention are described further herein.

DETAILED DESCRIPTION OF THE INVENTION

Various documents including, for example, publications and patents, are recited throughout this disclosure. All such documents are hereby incorporated by reference.

All percentages and ratios are calculated by weight unless otherwise indicated. All percentages and ratios are calculated based on the total composition unless otherwise indicated.

Referenced herein are trade names for components including various ingredients utilized in the present invention. The inventors herein do not intend to be limited by materials under a certain trade name. Equivalent materials (e.g., those obtained from a different source under a different name or reference number) to those referenced by trade name may be substituted and utilized in the descriptions herein.

As used herein, wherein any variable, moiety, group, or the like occurs more than one time in any variable or structure, its definition at each occurrence is independent of its definition at every other occurrence.

In the description of the invention various embodiments and/or individual features are disclosed. As will be apparent to the ordinarily skilled practitioner, all combinations of such embodiments and features are possible and can result in preferred executions of the present invention.

The compositions herein may comprise, consist essentially of, or consist of any of the elements as described herein.

While various embodiments and individual features of the present invention have been illustrated and described, various other changes and modifications can be made without departing from the spirit and scope of the invention. As will be also be apparent, all combinations of the embodiments and features taught in the foregoing disclosure are possible and can result in preferred executions of the invention.

As used herein, "alkenyl" is an unsubstituted or substituted hydrocarbon chain radical having from 2 to about 24 carbon atoms. Unless otherwise specified herein (for example, with respect to the "R" radical described below), more preferred alkenyl radicals have from 2 to about 10 carbon atoms; more preferably from 2 to about 8 carbon atoms, and most preferably from about 2 to about 6 carbon atoms. Alkenyl radicals have at least one carbon-carbon double bond. Non-limiting examples of alkenyl radicals include vinyl, allyl, and butenyl.

As used herein, "alkoxy" is an oxygen radical having an alkyl, alkenyl, or alkynyl, preferably an alkyl or alkenyl, and most preferably an alkyl substituent. Examples of alkoxy radicals include —O-alkyl and —O-alkenyl. An alkoxy radical may be substituted or unsubstituted.

As used herein, "alkyl" is an unsubstituted or substituted saturated hydrocarbon chain radical having from 1 to about 24 carbon atoms. Unless otherwise specified herein (for example, with respect to the "R" radical described below), more preferred alkyl radicals have from 1 to about 10 carbon atoms; more preferably from 1 to about 6 carbon atoms; and most preferably from 1 to about 4 carbon atoms. Preferred alkyl radicals include, for example, methyl, ethyl, propyl, iso-propyl, and butyl.

As used herein, "alkynyl" is an unsubstituted or substituted hydrocarbon chain radical having from 2 to about 24 carbon atoms. Unless otherwise specified herein (for example, with respect to the "R" radical described below), more preferred alkynyl radicals have from 2 to about 10 carbon atoms; more preferably from 2 to about 8 carbon atoms, and most preferably from about 2 to about 6 carbon atoms. Alkynyl radicals have at least one carbon-carbon triple bond.

As used herein, the term "animal" includes vertebrate animals, including mammals, such as humans and companion animals (e.g., domestic cats, dogs, horses, cows, or other similar animals), and most preferably humans.

As used herein, "heteroalkenyl" is a radical comprised of carbon atoms and one or more heteroatoms wherein the heteroatoms are selected from the group consisting of oxygen, sulfur, nitrogen, and phosphorous, more preferably, oxygen, sulfur, and nitrogen. Heteroalkenyl radicals comprise at least one carbon-carbon double bond. Unless otherwise specified herein, more preferred heteroalkenyl radicals have from 2 to about 10 carbon atoms; more preferably from 2 to about 8 carbon atoms, and most preferably from about 2 to about 6 carbon atoms. Heteroalkenyl radicals may be substituted or unsubstituted.

As used herein, "heteroalkyl" is a radical comprised of at least one carbon atom and one or more heteroatoms wherein the heteroatoms are selected from the group consisting of oxygen, sulfur, nitrogen, and phosphorous, more preferably, oxygen, sulfur, and nitrogen. Heteroalkyl radicals do not contain any carbon-carbon double bonds or carbon-carbon triple bonds. Unless otherwise specified herein, more preferred heteroalkyl radicals have from 1 to about 10 carbon atoms; more preferably from 2 to about 8 carbon atoms, and most preferably from about 2 to about 6 carbon atoms. Heteroalkyl radicals may be substituted or unsubstituted.

As used herein, "heteroalkynyl" is a radical comprised of carbon atoms and one or more heteroatoms wherein the heteroatoms are selected from the group consisting of oxygen, sulfur, nitrogen, and phosphorous, more preferably, oxygen, sulfur, and nitrogen. Heteroalkynyl radicals comprise at least one carbon-carbon triple bond. Unless otherwise specified herein, more preferred heteroalkynyl radicals have from 2 to about 10 carbon atoms; more preferably from 2 to about 8 carbon atoms, and most preferably from about 2 to about 6 carbon atoms. Heteroalkynyl radicals may be substituted or unsubstituted.

As used herein, a "salt" is a compound formed by at least partial neutralization of an acid by a base, or at least partial neutralization of a base by an acid. Salts may be organic or inorganic. Many such salts are known in the art. Examples include sodium stearate, calcium carbonate and octadecylamine hydrochloride.

As used herein unless otherwise specified, the term "substituted" in reference to a group, moiety, or the like, means having one or more pendant substituent groups each independently selected from alkyl, alkenyl, alkoxy, hydroxy, oxo, nitro, amino, alkylamino, cyano, halo, carboxy, alkoxyacyl (e.g., carboethyoxy), thiol, imino, thioxo, and hydroxyalkyl, preferably alkyl, alkenyl, alkoxy, hydroxy, oxo, nitro, amino, alkylamino, and halo, more preferably alkyl, alkenyl, alkoxy, hydroxy, nitro, amino, alkylamino, and halo, even more preferably alkyl, and alkoxy, and most preferably alkoxy.

As used herein, the term "unsubstituted" means not substituted.

As used herein, the term "lipid" refers to fats, oils, triglycerides, diglycerides, monoglycerides, and the like.

As used herein, the terms "lipophilic substance", "lipophilic compound" and the like refer to any material that is substantially non-polar in character. Non-limiting examples of such materials include cholesterol, pesticides such as DDT, tocopherol, terpenes, and the like. Such materials will typically have an octanol/water partition coefficient of greater than 1, as measured according to the method described in Hansch, C. and Leo, A. J., "Substituent Constants for Correlation Analysis in Chemistry and Biology," John Wiley & Sons, New York (1979).

As used herein, "pharmaceutically-acceptable" with reference to a given material means that the material is suitable for use in the animal intended for treatment without undue risks in terms of safety to the animal. Those of ordinary skill will be able to determine whether a given material is pharmaceutically-acceptable.

As used herein, "safe and effective amount" of a referenced material means an amount of such referenced material that is effective to exhibit biological or other activity, without undue adverse side effects (such as toxicity, irritation, or allergic response), commensurate with a reasonable benefit/risk ratio when used in the manner of this invention. The specific "safe and effective amount" will, obviously, vary considering such factors as the particular condition being treated, the physical condition of the treated animal, the size and weight of the treated animal, the duration of treatment, the nature of concurrent therapy (if any), the specific dosage form to be used, other components in the composition, and the dosage regimen desired for the composition. Those of ordinary skill will be able to determine whether the safe and effective amount.

Compositions of the Present Invention

The present invention relates to compositions suitable for a variety of benefits including, for example, ameliorating the undesirable side effects associated with compounds such as lipase inhibitors. In particular, one embodiment of the present invention relates to compositions which are suitable for administration to an animal for the purpose of stiffening one or more lipophilic substances present in the gastrointestinal tract of the animal, wherein the composition comprises a safe and effective amount of a stiffening agent as described herein. As used throughout, stiffening such lipophilic substances includes increasing the viscosity of the substance in vivo, resulting in the formation of solids, semi-solids, pastes, gels, and the like such that the foregoing side effects are ameliorated upon administration of the composition. Without intending to be limited by theory, it is believed that the present compositions are useful for inducing the formation of such stiffened materials, thereby ameliorating the side effects associated with undigested unstiffened fats, oils, other lipids, or other lipophilic substances, where such side effects may include anal leakage, loose stools, and the like.

Another embodiment of the present invention relates to compositions comprising:
  (a) a stiffening agent having a complete melting point of about 33° C. or greater which is selected from the group consisting of R—COOR', R—OR', R—CONR'R", R—NR'R", salts thereof, and mixtures thereof, wherein:
    (i) R is selected from the group consisting of alkyl radicals having from about 14 to about 24 carbon atoms, alkenyl radicals having from about 14 to about 24 carbon atoms, alkynyl radicals having from about 14 to about 24 carbon atoms, heteroalkyl radicals having from about 14 to about 24 carbon atoms, heteroalkenyl radicals having from about 14 to about 24 carbon atoms, and heteroalkynyl radicals having from about 14 to about 24 carbon atoms; and
    (ii) R' and R" are each, independently, selected from hydrogen, alkyl radicals, alkenyl radicals, alkynyl radicals, heteroalkyl radicals, heteroalkenyl radicals, and heteroalkynyl radicals; and
  (b) a lipase inhibitor;
wherein the ratio of the stiffening agent to the lipase inhibitor, by weight, is at least about 1:1.

The Stiffening Agent

The stiffening agent has a complete melting point of about 33° C. or greater. It is recognized that certain materials will have ranges of melting points and, further, that wherein the stiffening agent is a mixture of components the stiffening agent will also have a range of melting points. For purposes of this invention, the aforementioned "complete melting point" refers to the melting point at which the stiffening agent (including stiffening agents which are mixtures of components)

is completely melted, utilizing standard conditions well-known to one of ordinary skill.

Preferred stiffening agents often include those having a complete melting point of about 37° C. or greater, 42° C. or greater, 50° C. or greater, or 60° C. or greater. Often, preferred stiffening agents include those having a complete melting point of from about 33° C. to about 100° C., from about 33° C. to about 90° C., from about 33° C. to about 80° C., or from about 33° C. to about 70° C. Alternatively, the lower limits of each of these ranges may be substituted with about 42° C., about 50° C., or about 60° C.

The stiffening agent is selected from R—COOR', R—OR', R—CONR'R", R—NR'R", salts thereof, and mixtures thereof, wherein:
 (i) R is selected from the group consisting of alkyl radicals having from about 14 to about 24 carbon atoms, alkenyl radicals having from about 14 to about 24 carbon atoms, alkynyl radicals having from about 14 to about 24 carbon atoms, heteroalkyl radicals having from about 14 to about 24 carbon atoms, heteroalkenyl radicals having from about 14 to about 24 carbon atoms, and heteroalkynyl radicals having from about 14 to about 24 carbon atoms; and
 (ii) R' is selected from the group consisting of hydrogen, alkyl radicals, alkenyl radicals, alkynyl radicals, heteroalkyl radicals, heteroalkenyl radicals, and heteroalkynyl radicals.

In a more preferred embodiment herein, the stiffening agent is selected from R—COOR', salts thereof, and mixtures thereof. In an even more preferred embodiment herein, the stiffening agent is selected from R—COOH, salts thereof, and mixtures thereof. In a particularly preferred embodiment, the stiffening agent is a salt of R—COOH.

As used herein, the stiffening agent has a complete melting point of about 33° C. or greater. It is recognized that certain materials will have ranges of melting points and, further, that wherein the stiffening agent is a mixture of components the stiffening agent will also have a range of melting points. For purposes of this invention, the aforementioned "complete melting point" refers to the melting point at which the stiffening agent (including stiffening agents which are mixtures of components) is completely melted, utilizing standard conditions well-known to one of ordinary skill.

Preferred stiffening agents often include those having a complete melting point of about 37° C. or greater, 42° C. or greater, 50° C. or greater, or 60° C. or greater. Often, preferred stiffening agents include those having a complete melting point of from about 33° C. to about 100° C., from about 33° C. to about 90° C., from about 33° C. to about 80° C., or from about 33° C. to about 70° C. Alternatively, the lower limits of each of these ranges may be substituted with about 42° C., about 50° C., or about 60° C.

Wherein the stiffening agent is R—COOR', preferred stiffening agents include fatty acids (i.e., components in which R' is hydrogen). Fatty acids are commonly known in the art, and will be understood by one of ordinary skill. The fatty acid utilized may not be limited, provided the stiffening agent has the melting point described above. In this preferred embodiment, the stiffening agent may be depicted as follows:

R—COOH wherein "R" is a fatty acid chain which is a saturated or unsaturated chain having from about 14 to about 24 carbon atoms, and wherein "COOH" is a carboxylic acid moiety. More preferably in this embodiment, "R" is a saturated or unsaturated chain having from about 18 to about 24, most preferably from about 18 to about 22 carbon atoms. Also preferably, the fatty acid chain is fully saturated (having zero double or triple bonds), or contains 1 double bond. Most preferably, the fatty acid chain is saturated, i.e. having zero double or triple bonds.

Preferred fatty acids include myristic acid, pentadecanoic acid, palmitic acid, margaric acid, stearic acid, elaidic acid, eleostearic acid, licanic acid, arachidic acid, eicosenoic acid, behenic acid, erucic acid, lignoceric acid, and mixtures thereof or, alternatively, myristic acid, pentadecanoic acid, palmitic acid, margaric acid, elaidic acid, eleostearic acid, licanic acid, arachidic acid, eicosenoic acid, behenic acid, erucic acid, lignoceric acid, and mixtures thereof. Among these, particularly preferred long chain fatty acids include palmitic acid, stearic acid, arachidic acid, behenic acid, and mixtures thereof or, alternatively, palmitic acid, arachidic acid, behenic acid, and mixtures thereof. Behenic acid is particularly preferred.

In another preferred embodiment wherein the stiffening agent is R—COOR' and wherein R' is selected from alkyl radicals, alkenyl radicals, alkynyl radicals, heteroalkyl radicals, heteroalkenyl radicals, and heteroalkynyl radicals (and R is defined as above), the stiffening agent is preferably an ester of the aforementioned fatty acid. Esters of fatty acids will also be well-known to one of ordinary skill in the art. Again, the ester of the fatty acid may not be limited, provided the stiffening agent has the melting point described above.

In this preferred embodiment, R' may be a straight (for example, n-propyl) or branched (for example, iso-propyl) chain. Highly preferred R' groups include methyl, ethyl, n-propyl, iso-propyl, n-butyl, and iso-butyl groups, and mixtures thereof. Ethyl groups are particularly preferred.

In another preferred embodiment wherein the stiffening agent is depicted as R—OR', the stiffening agent is preferably a fatty alcohol (i.e., compounds in which R' is hydrogen and (and R is defined as above). Fatty alcohols are commonly known in the art, and will be understood by one of ordinary skill. The fatty alcohol utilized may not be limited, provided the stiffening agent has the melting point described above. In this preferred embodiment, the stiffening agent may be depicted as follows:

R—OH wherein "R" is a fatty acid chain which is a saturated or unsaturated chain having from about 14 to about 24 carbon atoms, and wherein "OH" is a hydroxyl moiety. More preferably in this embodiment, "R" is a saturated or unsaturated chain having from about 18 to about 24, most preferably from about 18 to about 22 carbon atoms. Also preferably, the fatty alcohol chain is alkyl or alkenyl. Most preferably, the fatty alcohol chain is alkyl. Preferred fatty alcohols include palmityl alcohol and stearyl alcohol.

Other stiffening agents which are depicted as R—OR', but wherein R' is selected from alkyl radicals, alkenyl radicals, alkynyl radicals, heteroalkyl radicals, heteroalkenyl radicals, and heteroalkynyl radicals; (and R is defined as above), include, preferably, ethers of the aforementioned fatty alcohols. The ethers of the fatty alcohols will also be well-known in the art. Again, the ether of the fatty alcohol may not be limited, provided the stiffening agent has the melting point described above.

In a particularly preferred embodiment wherein the stiffening agent is an ether, R' is a straight or branched chain of carbon atoms, preferably containing from 1 to about 24 carbon atoms. Even more preferably, R' contains from 1 to about 22 carbon atoms and, again, may be a straight (for example, n-propyl) or branched (for example, iso-propyl) chain. Highly preferred R' groups include methyl, ethyl, n-propyl, iso-propyl, n-butyl, iso-butyl groups, and mixtures thereof. Ethyl groups are particularly preferred.

Examples of preferred ethers include stearyl methyl ether, stearyl ethoxy ether (i.e., the ethylene glycol adduct of stearyl alcohol), and cetyl ethoxy ether (i.e., the ethylene glycol adduct of cetyl alcohol).

In one embodiment herein, the stiffening agent is R—CONR'R", wherein R is defined as above and R' and R" are each, independently, selected from hydrogen, alkyl radicals, alkenyl radicals, alkynyl radicals, heteroalkyl radicals, heteroalkenyl radicals, and heteroalkynyl radicals. Such an amide may not be limited, provided the stiffening agent has the melting point described above. A non-limiting example includes erucamide. Most preferably in this embodiment, at least one of R' and R" is not hydrogen.

Other stiffening agents are depicted as R—NR'R". R' and R" are each, independently, selected from hydrogen, alkyl radicals, alkenyl radicals, alkynyl radicals, heteroalkyl radicals, heteroalkenyl radicals, and heteroalkynyl radicals (and R is defined as above). Accordingly, the amine can be a primary, secondary, or tertiary amine. Again, the amine may not be limited, provided the stiffening agent has the melting point described above. Most preferably in this embodiment, at least one of R' and R" is not hydrogen. A non-limiting example of a preferred amine includes octadecylamine.

Wherein the stiffening agent is a salt, the stiffening agent is a pharmaceutically-acceptable salt. Such salts will be well-known to the ordinarily skilled artisan. Again, the salt may not be limited, provided the stiffening agent has the melting point described above.

Particularly preferred salts herein include salts of the aforementioned fatty acids. For example, such salts can include those salts of myristic acid, pentadecanoic acid, palmitic acid, palmitoleic acid, margaric acid, stearic acid, oleic acid, elaidic acid, eleostearic acid, licanic acid, arachidic acid, eicosenoic acid, behenic acid, erucic acid, lignoceric acid, and mixtures thereof. Among these, salts of palmitic acid, stearic acid, arachidic acid, behenic acid, and mixtures thereof are particularly preferred.

To illustrate, preferred salts include, for example, aluminum salts and zinc salts, as well as alkali metal salts such as sodium salts, and potassium salts, or alkaline earth metal salts such as magnesium salts and calcium salts. Magnesium salts, sodium salts, calcium salts, or aluminum salts are particularly preferred herein. Among these, calcium salts and aluminum salts are often most preferred. The salts are most preferably selected from calcium stearate, calcium behenate, calcium arachidate, calcium palmitate, magnesium stearate, magnesium behenate, magnesium arachidate, magnesium palmitate, aluminum stearate, aluminum behenate, aluminum arachidate, aluminum palmitate, zinc stearate, zinc behenate, zinc arachidate, zinc palmitate, and mixtures thereof. Calcium stearate is particularly preferred herein.

The stiffening agent is preferably included in a composition described herein at a level that is safe and effective for the particular purpose and animal being treated. As such, these levels will be readily understood by one of ordinary skill in the art. In a preferred embodiment herein, the compositions or kits will comprise the stiffening agent based upon a weight ratio to lipase inhibitor which is described herein below (e.g., by weight, preferably at least about 1:1 based on stiffening agent to lipase inhibitor).

Additionally, a given composition may optionally comprise at least about 0.1%, at least about 0.2%, at least about 0.5%, at least about 0.8%, or at least about 1%, or at least about 5% of the stiffening agent, by weight of the composition. In other preferred compositions, the compositions may optionally comprise from about 0.1% to about 99%, from about 0.2% to about 95%, from about 0.5% to about 95%, from about 0.8% to about 95%, or from about 1% to about 95%, or from about 5% to about 95% of the stiffening agent, all by weight of the composition. In particularly preferred embodiments, wherein a lipase inhibitor is present in a given composition or kit, such levels of stiffening agent will be consistent with the preferred ratios of stiffening agent to lipase inhibitor, as described herein below.

As an adjunct to the stiffening agent, it may often be preferred to include one or more pharmaceutically-acceptable salts in the compositions. For example, wherein the stiffening agent comprises a fatty acid, it has been found that wherein the compositions or kits further comprise a pharmaceutically-acceptable salt, the salt may form an insoluble material (this may be described for simplicity as an "insoluble soap") with the fatty acid in situ after ingestion. Such insoluble materials, formed in situ, may further assist with stiffening the lipophilic substances present in the gastrointestinal tract. Accordingly, a given composition herein may optionally comprise one or more pharmaceutically-acceptable salts which are distinct from the stiffening agent. Such salts will be well-known to one or ordinary skill. As examples, certain salts will include calcium carbonate, calcium citrate, calcium phosphate, calcium chloride, calcium citrate-malate, magnesium carbonate, zinc acetate, and the like. Wherein a salt is present in a given composition, the composition may optionally comprise from about 0.01% to about 70%, more preferably 1% to about 60%, and most preferably from about 5% to about 50% of the pharmaceutically-acceptable salt, all by weight of the composition.

The Lipase Inhibitor

The lipase inhibitor utilized in certain embodiments of this invention will be readily understood by one of ordinary skill in the art. As an example, one or more of various lipase inhibitors may optionally be included in the present compositions, or otherwise administered in conjunction with the present compositions (e.g., contemporaneously with the present compositions or at predetermined times relative to administration of the compositions).

Lipase inhibitors effectively produce in situ undigested fat and/or oil that can dissolve lipophilic toxins and hasten their elimination from the body. Such lipase inhibitors have been demonstrated as useful for the treatment or prevention of obesity, Type II Diabetes, or other like benefits. Examples of such compounds include tetrahydrolipstatin (orlistat; commercially available from F. Hoffman-La Roche Ltd, Basel, Switzerland as the drug substance in XENICAL®) and its derivatives (e.g., lipstatin) described in U.S. Pat. No. 4,598,089, Hadvary et al., issued Jul. 1, 1986, including tetrahydrolipstatin, having the following structure:

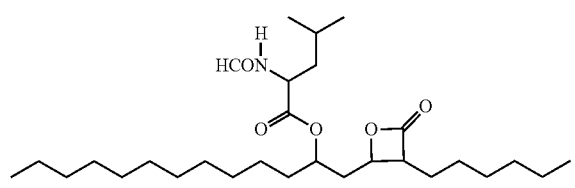

and also including lipstatin, having the following structure:

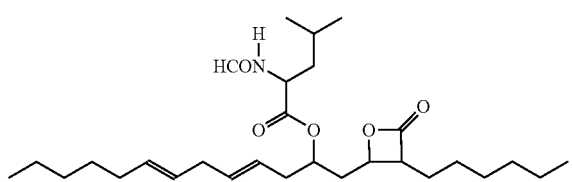

Other non-limiting examples of lipase inhibitors include 2-amino4H-3, 1-benzoxazin-4-one and its derivatives as described in WO 00/40247 published Jul. 13, 2000; 2-oxy-4H-3,1-benzoxazin-4-ones and its derivatives as described in WO 00/40569, published Jul. 13, 2000; and 2-thio-4H-3,1-benzoxazin-4-one and its derivatives as described in WO 01/53278, published Jul. 26, 2001. These will advantageously include ATL-962 and related compounds (Alizyme Therapeutics Limited) as described in U.S. Pat. No. 6,624,161, as well as other lipase inhibitors as described in WO 00/40569.

In particular, illustrative examples described in U.S. Pat. No. 6,624,161 include 2-ethoxy-6-methyl-4H-3,1-benzoxazin-4-one; 2-phenoxy-4H-3,1-benzoxazin-4-one; 2-(4-methoxy-phenoxy)-4H-3,1-benzoxazin-4-one; 2-(4-methylphenoxy)-4H-3,1-benzoxazin-4-one; 2-(2-chloroethoxy)-4H-3,1-benzoxazin-4-one; 2-propoxy-4H-3,1-benzoxazin-4-one; 6-methyl-2-phenoxy-4H-3,1-benzoxazin-4-one; 6-methyl-2-propoxy-4H-3,1-benzoxazin-4-one; 2-(2-ethylhexyloxy)-4H-3,1-benzoxazin-4-one; 6-methyl-2-octyloxy-4H-3,1-benzoxazin-4-one; 2-hexyloxy-6-methyl-4H-3,1-benzoxazin-4-one; 2-(2-ethylhexyloxy)-6-methyl-4H-3,1-benzoxazin-4-one; 6-ethyl-2-hexyloxy-4H-3,1-benzoxazin-4-one; 2-decyloxy-6-methyl-4H-3,1-benzoxazin-4-one; 6-methyl-2-tetadecyloxy-4H-3,1-benzoxazin-4-one; 6-methyl-2-pentadecyloxy-4H-3,1-benzoxazin-4-one; 2-hexadecyloxy-6-methyl-4H-3,1-benzoxazin-4-one; 2-heptadecyloxy-6-methyl-4H-3,1-benzoxazin-4-one; 6-methyl-2-octadecyloxy-4H-3,1-benzoxazin-4-one; 7-ethyl-2-hexyloxy-4H-3,1-benzoxazin-4-one; 2-(3,7-dimethyloctyloxy)-6-methyl-4H-3,1-benzoxazin-4-one; 2-[2-(2-hexyloxyethoxy)ethoxy-6-methyl-4H-3,1-benzoxazin-4-one; (Z)-6-methyl-2-(octadeca-9-enyloxy)-4H-3,1-benzoxazin-4-one; 6-methyl-2-(10-phenyldecyloxy)-4H-3,1-benzoxazin-4-one; 7-ethyl-2-octyloxy-4H-3,1-benzoxazin-4-one; 2-octyloxy-4H-3,1-benzoxazin-4-one; 6-methoxy-2-octyloxy-4H-3,1-benzoxazin-4-one; 6-methyl-2-(4-phenoxyphenoxy)-4H-3,1-benzoxazin-4-one; 2-hexyloxy-4H-3,1-benzoxazin-4-one; 2-docecyloxy-6-methyl-4H-3,1-benzoxazin-4-one; 6-iodo-2-octyloxy-4H-3,1-benzoxazin-4-one; 7-butyl-2-octyloxy-4H-3,1-benzoxazin-4-one; 6-methyl-2-(8-phenyloctyloxy)-4H-3,1-benzoxazin-4-one; 6-methyl-2-(4-phenylbutyloxy)-4H-3,1-benzoxazin-4-one; 6-methyl-2-(12-phenyldodecyloxy)-4H-3,1-benzoxazin-4-one; (Z)-6-methyl-2-(octadeca-11-enyloxy)4H-3,1-benzoxazin-4-one; 6-methyl-2-(octadeca-11-ynyloxy)-4H-3,1-benzoxazin-4-one; 6-methyl-2-[-10-(thien-2-yl)-decyloxy]-4H-3,1-benzoxazin-4-one; 5-fluoro-2-hexadecyloxy-4H-3,1-benzoxazin-4-one; 8-fluoro-2-hexadecyloxy-4H-3,1-benzoxazin-4-one; 6-fluoro-2-hexadecyloxy-4H-3,1-benzoxazin-4-one; 6-chloro-2-hexadecyloxy-4H-3,1-benzoxazin-4-one; 6-cyclopropyl-2-hexadecyloxy-4H-3,1-benzoxazin-4-one; 2-hexadecyloxy-6-hydroxy-4H-3,1-benzoxazin-4-one; 2-hexadecyloxy-6-mercapto-4H-3,1-benzoxazin-4-one; 6-amino-2-hexadecyloxy-4H-3,1-benzoxazin-4-one; 2-hexadecyloxy-6-nitro-4H-3,1-benzoxazin-4-one; 6-cyano-2-hexadecyloxy-4H-3,1-benzoxazin-4-one; 2-hexadecyloxy-6-trifluoromethyl-4H-3,1-benzoxazin-4-one; 6-formyl-2-hexadecyloxy-4H-3,1-benzoxazin-4-one; 6-acetamido-2-dexadecyloxy-4H-3,1-benzoxazin-4-one; 2-hexadecyloxy-6-sulfo-4H-3,1-benzoxazin-4-one; 2-hexadecyloxy-7-trifluoromethyl-4H-3,1-benzoxazin-4-one; 2-hexadecyloxy-7-hydroxy-4H-3,1-benzoxazin-4-one; 7-amino-2-hexadecyloxy-4H-3,1-benzoxazin-4-one; 7-cyclopropyl-2-hexadecyloxy-4H-3,1-benzoxazin-4-one; 7-chloro-2-hexadecyloxy-4H-3,1-benzoxazin-4-one; 2-hexadecyloxy-4H-pyrido[2,3-d] [1,3]oxazin-4-one; (E)-2-(hexadeca-5-enyloxy)-4H-3,1-benzoxazin-4-one; 2-(2-naphthyloxy)-4H-3,1-benzoxazin-4-one; 2-(3-pyridyloxy)-4H-3,1-benzoxazin-4-one; 2-(2-pyrrolyloxy)-4H-3,1-benzoxazin-4-one; 2-(2-piperidinyl-oxy)-4H-3,1-benzoxazin-4-one; 2-[6-(2-pyrrol)yl-hexyloxy]-4H-3,1-benzoxazin-4-one; 2-(14-cyanotetradecyloxy)-4H-3,1-benzoxazin-4-one; 2-(14-nitrotetradecyloxy)-4H-3,1-benzoxazin-4-one; 2-(15-methoxypentadecyloxy)-4H-3,1-benzoxazin-4-one; 2-(15-phenylpentadecyloxy)-4H-3,1-benzoxazin-4-one; 2-(14-aminotetradecyloxy)-4H-3,1-benzoxazin-4-one; 2-(14-hydroxytetradecyloxy)-4H-3,1-benzoxazin-4-one; 2-(12-N-methylcarbamoyldodecyloxy)-4H-3,1-benzoxazin-4-one; 2-hexadecyloxy-6,7-dimethyl-4H-3,1-benzoxazin-4-one; 5-methyl-2-octyloxy-4H-3,1-benzoxazin-4-one; 7-octyl-2-octyloxy-4H-3,1-benzoxazin-4-one; 6-octyl-2-octyloxy-4H-3,1-benzoxazin-4-one; 2-(5-chloropentyloxy)-6-methyl-4H-3,1-benzoxazin-4-one; 2,2'-(1,16-hexadecylidenedioxy)-bis-4H-3,1-benzoxazin-4-one; 6,8-dimethyl-2-octyloxy-4H-3,1-benzoxazin-4-one; 6-methyl-2-(6-phenoxyhexyloxy)-4H-3, 1-benzoxazin-4-one; and 6-methyl-2-[6-(4-phenoxyphenoxy)hexyloxy]4H-3,1-benzoxazin-4-one.

Preferred among these compounds include: 2-(4-methylphenoxy)-4H-3,1-benzoxazin-4-one; 2-(4-chlorophenoxy)-4H-3,1-benzoxazin-4-one; 6-methyl-2-phenoxy-4H-3,1-benzoxazin-4-one; 2-(2-ethylhexyloxy)-4H-3,1-benzoxazin-4-one; 6-methyl-2-octyloxy-4H-3,1-benzoxazin-4-one; 2-hexyloxy-6-methyl-4H-3,1-benzoxazin-4-one; 2-(2-ethyloxy)-6-methyl-4H-3,1-benzoxazin-4-one; 6-ethyl-2-hexyloxy-4H-3,1-benzoxazin-4-one; 7-ethyl-2-hexyloxy-4H-3, 1-benzoxazin-4-one; 7-ethyl-2-octyloxy-4H-3,1-benzoxazin-4-one; 2-octyloxy-4H-3,1-benzoxazin-4-one; 6-methoxy-2-octyloxy-4H-3,1-benzoxazin-4-one; 2-hexyloxy-4H-3,1-benzoxazin-4-one; 6-iodo-2-octyloxy-4H-3,1-benzoxazin-4-one; 7-butyl-2-octyloxy-4H-3,1-benzoxazin-4-one; 6-methyl-2-(8-phenyloctyloxy)-4H-3,1-benzoxazin-4-one; 6-methyl-2-(4-phenylbutyloxy)-4H-3,1-benzoxazin-4-one; and 5-methyl-2-octyloxy-4H-3,1-benzoxazin-4-one. Other preferred compounds include: 2-decyloxy-6-methyl-4H-3,1-benzoxazin-4-one; 6-methyl-2-tetadecyloxy-4H-3, 1-benzoxazin-4-one; 6-methyl-2-pentadecyloxy-4H-3,1-benzoxazin-4-one; 2-hexadecyloxy-6-methyl-4H-3,1-benzoxazin-4-one; 2-heptadecyloxy-6-methyl-4H-3,1-benzoxazin-4-one; 6-methyl-2-octadecyloxy-4H-3,1-benzoxazin-4-one; 2-(3,7-dimethyloctyloxy)-6-methyl-4H-3,1-benzoxazin-4-one; 2-[2-(2-hexyloxyethoxy)ethoxy-6-methyl-4H-3,1-benzoxazin-4-one; (Z)-6-methyl-2-(octadeca-9-enyloxy)-4H-3,1-benzoxazin-4-one; 6-methyl-2-(10-phenyldecyloxy)-4H-3,1-benzoxazin-4-one; 6-methyl-2-(4-phenoxyphenoxy)-4H-3,1-benzoxazin-4-one; 2-docecyloxy-6-methyl-4H-3,1-benzoxazin-4-one; 6-methyl-2-(12-phenyldodecyloxy)-4H-3,1-benzoxazin-4-one; (Z)-6-methyl-2-(octadeca-11-enyloxy)-4H-3,1-benzoxazin-4-one; 6-methyl-2-(octadeca-11-ynyloxy)-4H-3,1-benzoxazin-4-one; 6-methyl-2-[-10-(thien-2-yl)-decyloxy]-4H-3,1-benzoxazin-4-one; 7-octyl-2-octyloxy-4H-3,1-benzoxazin-4-one; 6-octyl-2-octyloxy-4H-3,1-benzoxazin-4-one; 2-(5-chloropentyloxy)-6-methyl-4H-3,1-benzoxazin- 4-one; 2,2'-(1,16-hexadecylidenedioxy)-bis-4H-3,1-benzoxazin-4-one; 6-methyl-2-(6-phenoxyhexyloxy)-4H-3,1-benzoxazin-4-one; and 6-methyl-2-[6-(4-phenoxyphenoxy)hexyloxy]-4H-3,1-benzoxazin-4-one. Among these, particularly preferred include: 2-decyloxy-6-methyl-4H-3,1-benzoxazin-4-one; 6-methyl-2-tetradecyloxy]-4H-3,1-benzoxazin-4-one; and 2-hexadecyloxy-6-methyl-4H-3,1-benzoxazin-4-one. Among these 2-hexadecyloxy-6-methyl-4H-3,1-benzoxazin-4-one is particularly preferred. As one of ordinary skill will recognize, all of these compounds will extend to the tautomers thereof, as well as (but not limited to) pharmaceutically acceptable salts, esters, amides or prodrugs thereof.

Other non-limiting examples of lipase inhibitors include teasaponin described in Han et al., *Int. J. Obes. Relat. Metab. Disord.*, Vol. 25, pp. 1459-1464, 2001; long-chain alpha-keto amides described in Chiou et al., *Lipids*, Vol. 36, pp. 535-542, 2001; extract of Nomame Herba described in Yamamoto et al., *Int. J. Obes. Relat. Metab. Disord.*, Vol. 24, pp. 758-764, 2000; chiral alkylphosphonates described in Cavalier et al., "*Chem. Phys. Lipids,*" Vol. 100, pp. 3-31, 1999; chiral isomers of beta-lactone described in Tomoda et al., *Biochem. Biophys. Res. Commun.*, Vol. 265, pp. 536-540, 1999; and Pluronicy L-101 described in Comai et al., *Int. J. Obes.*, Vol. 4, pp. 33-42, 1980.

Wherein a lipase inhibitor is utilized, the lipase inhibitor is preferably included in a given composition at a level that is safe and effective for the particular purpose and animal being treated. As such, these levels will be readily understood by one of ordinary skill in the art. In a preferred embodiment herein, the compositions or kits will comprise the lipase inhibitor based upon a weight ratio to relative to stiffening agent which is described herein below (e.g., by weight, preferably at least about 4.5:1 based on stiffening agent to lipase inhibitor).

Alternatively or additionally, a given composition may optionally comprise at least about 0.001%, at least about 0.002%, at least about 0.005%, at least about 0.01%, at least about 0.05%, or at least about 0.1% of the lipase inhibitor, by weight of the relevant composition. In other preferred compositions, the compositions may optionally comprise from about 0.001% to about 15%, from about 0.002% to about 10%, from about 0.005% to about 4%, from about 0.01% to about 2%, or from about 0.1% to about 1% of the lipase inhibitor, by weight of the composition. In particularly preferred embodiments, wherein a lipase inhibitor is present in a given composition or kit, such levels of lipase inhibitor will be consistent with the preferred ratios of stiffening agent to lipase inhibitor, as described herein below.

The Ratio of Stiffening Agent to Lipase Inhibitor

In preferred embodiments herein, compositions or kits will comprise the stiffening agent and lipase inhibitor at a ratio, by weight, which is at least about 1:1 based on stiffening agent to lipase inhibitor. In particularly preferred embodiments, such ratios will be consistent with the preferred levels of stiffening agent and lipase inhibitor, respectively, described herein above.

In other preferred embodiments, the ratio of the stiffening agent to the lipase inhibitor, by weight, is at least about 2:1, alternatively at least about 3:1, alternatively at least about 4:1, alternatively at least about 4.5:1, alternatively at least about 5:1, alternatively at least about 6:1, also alternatively at least about 7:1, or also alternatively at least about 8:1. In still other preferred embodiments, the ratio of the stiffening agent to the lipase inhibitor, by weight, is from about 1:1 to about 100:1, alternatively from about 2:1 to about 100:1, alternatively from about 3:1 to about 100:1, alternatively from about 4:1 to about 100:1, alternatively from about 4.5:1 to about 100:1, alternatively from about 5:1 to about 75:1, alternatively from about 6:1 to about 50:1, alternatively from about 7:1 to about 40:1, or also alternatively from about 8:1 to about 30:1.

Kits of the Present Invention

In certain embodiments of the present invention, the stiffening agent and lipase inhibitor may be formulated in separately dosable compositions, e.g., as separate dosage forms that are co-packaged, for example, within a containment device. This embodiment may be useful for simplifying formulation issues, or for sequential dosing of a given component. Accordingly, as an additional embodiment of the present invention, kits are provided which comprise:

(a) a first composition comprising a stiffening agent having a complete melting point of about 33° C. or greater which is selected from the group consisting of R—COOR', R—OR', R—CONR'R", R—NR'R", salts thereof, and mixtures thereof, wherein:
  (i) R is selected from the group consisting of alkyl radicals having from about 14 to about 24 carbon atoms, alkenyl radicals having from about 14 to about 24 carbon atoms, alkynyl radicals having from about 14 to about 24 carbon atoms, heteroalkyl radicals having from about 14 to about 24 carbon atoms, heteroalkenyl radicals having from about 14 to about 24 carbon atoms, and heteroalkynyl radicals having from about 14 to about 24 carbon atoms; and
  (ii) R' and R" are each, independently, selected from the group consisting of hydrogen, alkyl radicals, alkenyl radicals, alkynyl radicals, heteroalkyl radicals, heteroalkenyl radicals, and heteroalkynyl radicals; and
(b) a second composition comprising a lipase inhibitor.

As with any of a variety of other optional components, the kits may optionally comprise the non-digestible, non-absorbable, open-celled polymeric foam described herein below.

In yet a further embodiment of the present composition, other kits may comprise:

(a) a composition comprising a stiffening agent having a complete melting point of about 33° C. or greater which is selected from the group consisting of R—COOR', R—OR', R—CONR'R", R—NR'R", salts thereof, and mixtures thereof, wherein:
  (i) R is selected from the group consisting of alkyl radicals having from about 14 to about 24 carbon atoms, alkenyl radicals having from about 14 to about 24 carbon atoms, alkynyl radicals having from about 14 to about 24 carbon atoms, heteroalkyl radicals having from about 14 to about 24 carbon atoms, heteroalkenyl radicals having from about 14 to about 24 carbon atoms, and heteroalkynyl radicals having from about 14 to about 24 carbon atoms; and
  (ii) R' and R" are each, independently, selected from the group consisting of hydrogen, alkyl radicals, alkenyl radicals, alkynyl radicals, heteroalkyl radicals, heteroalkenyl radicals, and heteroalkynyl radicals; and
(b) optionally, a lipase inhibitor; and
(c) information associated with the composition that use of the composition will provide one or more benefits selected from treatment of gastrointestinal distress, treatment of fecal urgency, treatment of obesity, weight loss, weight control, treatment of hyperlipidemia, treatment of diarrhea, inhibition of anal leakage, reduction of levels of toxic substances, treatment of Type II Diabetes, delay of onset of Type II Diabetes, prevention of Type II Diabetes, and combinations thereof.

As with any of a variety of other optional components, the kits may also optionally comprise the non-digestible, non-absorbable, open-celled polymeric foam described herein below. Preferably, the information of the kit indicates that one of the benefits described herein will result when the compositions are used in accordance with instructions for use.

In yet a further embodiment, the present kits include aids for improving compliance with regard to administration of compositions of the present invention. In this embodiment, the kits may comprise:

(a) a stiffening agent having a complete melting point of about 33° C. or greater which is selected from the group consisting of R—COOR', R—OR', R—CONR'R", R—NR'R", salts thereof, and mixtures thereof, wherein:
  (i) R is selected from the group consisting of alkyl radicals having from about 14 to about 24 carbon atoms, alkenyl radicals having from about 14 to about 24 carbon atoms, alkynyl radicals having from about 14 to about 24 carbon atoms, heteroalkyl radicals having from about 14 to about 24 carbon atoms, heteroalkenyl radicals having from about 14 to about 24 carbon atoms, and heteroalkynyl radicals having from about 14 to about 24 carbon atoms; and
  (ii) R' and R" are each, independently, selected from the group consisting of hydrogen, alkyl radicals, alkenyl radicals, alkynyl radicals, heteroalkyl radicals, heteroalkenyl radicals, and heteroalkynyl radicals; and
(b) optionally, a lipase inhibitor; and
(c) directions or instructions for use.

As with any of a variety of other optional components, the kits may also optionally comprise the non-digestible, non-absorbable, open-celled polymeric foam described herein below.

As examples, such directions or instructions for use may include recommended size and frequency of dose, maximum allowable dose, and/or any contraindications. As a particularly preferred example, such kits may include blister cards wherein each card comprises the total daily dose of the composition to be administered by the user. The blister cards may be divided into sections, usually by perforations wherein each dose section of the blister card comprises a prescribed amount or dose of the composition alone or, for example, with one or more lipase inhibitors either integral to the composition of the present invention or completely separate. See e.g., WO 9822072, published May 28, 1998.

Optional Components and Forms of the Compositions and Kits Herein

The various compositions described herein may contain one or more optional components suitable for advancing their utility with respect to the treatments described herein, for example, treating gastrointestinal distress, treating fecal urgency, treating obesity, treating hyperlipidemia, treating diarrhea, inhibiting anal leakage, reducing levels of toxic substances (in, for example, the gastrointestinal tract), reducing blood cholesterol levels, inducing satiety, effecting weight loss, effecting weight control, treating Type II Diabetes, delaying onset of Type II Diabetes, preventing Type II Diabetes, and combinations thereof in an animal. For example, various optional components may assist with improving ease of formulation, stability, palatability, appearance, or other like qualities of the relevant composition.

Preferably, the compounds of the present invention are formulated into compositions for use in treatment of conditions such as the foregoing. Standard formulation techniques are used, such as those disclosed in *Remington's Pharmaceutical Sciences*, Mack Publishing Company, Easton, Pa. (1990).

The composition may be administered in any convenient form including, for example, a capsule, pill, caplet, tablet, chewable tablet, suspension, suppository, or the like. For example, any method or process for making a suitable dosage form may be employed wherein a mechanical device is employed to compress the foam into solid forms including capsules and tablets that utilize suitable binders and/or coatings that are known to those skilled in the art. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, effervescent preparations reconstituted from effervescent granules, suitable solvents, preservatives, emulsifying agents, suspending agents, diluents, sweeteners, melting agents, coloring agents, flavoring agents, or the like.

Orally administered compositions can also include liquid solutions, emulsions, suspensions, elixirs, tinctures, syrups, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Per-oral liquid compositions may also contain one or more components such as sweeteners, flavoring agents or colorants.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, EUDRAGIT coatings, waxes and shellac.

In all of the foregoing, of course, the components described herein can be administered alone or as mixtures, and the compositions may further include additional drugs or excipients as appropriate for the desired treatment or use.

In addition to a given component as described herein (e.g., the stiffening agent or lipase inhibitor), the compositions of the subject invention may contain a pharmaceutically-acceptable carrier. The term "pharmaceutically-acceptable carrier," as used herein, means one or more compatible solid or liquid filler diluents or encapsulating substances that are suitable for administration to an animal. The term "compatible," as used herein, means that these optional components are capable of being commingled with a component described herein (e.g., the stiffening agent or lipase inhibitor), and with each other, in a manner such that there is no interaction which would substantially reduce the efficacy of the composition under ordinary use situations. The pharmaceutically-acceptable carrier can itself be inert or it can possess functional benefits of its own.

In a preferred embodiment of the present invention, the compositions may incorporate an open-celled polymeric foam in accordance with WO 02/074343, published Sep. 26, 2002. In this embodiment, it is found that the ratio of stiffening agent to lipase inhibitor may not be important, as the open-celled polymeric foam is effective in combination with the stiffening agent to ameliorate the aforementioned side effects associated with the lipase inhibitor. In particular, in this embodiment, the present compositions may comprise:

(a) a stiffening agent having a complete melting point of about 33° C. or greater which is selected from the group consisting of R—COOR', R—OR', R—CONR'R", R—NR'R", salts thereof, and mixtures thereof, wherein:
  (i) R is selected from the group consisting of alkyl radicals having from about 14 to about 24 carbon atoms, alkenyl radicals having from about 14 to about 24 carbon atoms, alkynyl radicals having from about 14 to about 24 carbon atoms, heteroalkyl radicals having from about 14 to about 24 carbon atoms, heteroalkenyl radicals having from about 14 to about 24 carbon atoms, and heteroalkynyl radicals having from about 14 to about 24 carbon atoms; and
  (ii) R' and R" are each, independently, selected from the group consisting of hydrogen, alkyl radicals, alkenyl radicals, alkynyl radicals, heteroalkyl radicals, heteroalkenyl radicals, and heteroalkynyl radicals; and
(b) an non-digestible, non-absorbable, open-celled polymeric foam; and
(c) a lipase inhibitor.

Of course, the preferences with respect to stiffening agent and lipase inhibitor, as well as their respective levels and ratios in relation to each other may be as set forth above. Accordingly, for brevity these will not again be repeated. In addition, the open-celled polymeric foam is described in WO 02/074343, published Sep. 26, 2002, and the ordinarily skilled artisan will be able to incorporate such foams based on the disclosure therein. For convenience, however, the foams are described herein below, utilizing the following definitions:

As used herein, the term "absorb," with reference to a given material, refers to the process of transporting the material, or the breakdown products of the material from the lumen of the intestine into the enterocyte, regardless of whether the material is chemically altered or not, or whether it is metabolized or not. For example, "absorption" of the following materials refers to their transport across the intestinal wall: fats, oils, fatty acids, soaps, monoglycerides, triglycerides, polyglycerides, DDT, PCBs, phthalate esters, dioxins, carbon tetrachloride, cholesterol, and the like. The term "absorbable" refers to a material which is capable of being transported from the lumen through the intestinal wall, either in its chemically unaltered state (e.g., DDT) or after being chemically modified in the gastrointestinal tract (e.g., hydrolysis of fats and oils to form fatty acids and monoacylglycerol). Similarly, the terms "unabsorbable" and "non-absorbable" refer to materials which cannot be transported from the lumen of the intestine into the enterocyte and which cannot be chemically modified in the gastrointestinal tract under normal circumstances to form absorbable materials. Examples of "unabsorbable" or "non-absorbable" materials include, for example, those described in Miller et al., *Fundamental Applied Toxicology*, Vol. 24, pp. 229-237, 1995; and inulin, disclosed in Flamm et al., *Critical Rev. Food Science Nutrition*, Vol. 41(5), pp. 353-362, 2001.

As used herein, the term "non-digestible" means that the referenced material is not susceptible to degradation through the action of digestive enzymes.

As used herein, the term "sequester" used with reference to an open-celled polymeric foam means that a material is held within the pores of the polymeric foam via capillary forces, sorption of the material into the polymer itself (i.e., the struts), and/or adsorption onto the surface of the polymer.

The foams described in this optional embodiment are non-digestible and non-absorbable. In addition, the foams are open-celled. As used herein, a foam is "open-celled" if at least about 80% of the cells in the foam structure that are at least 1 µm in size are in unobstructed communication with at least one adjacent cell. Such cells will have intercellular openings or "windows" connecting one cell to the other within the foam structure.

The individual cells in such open-celled foams may be defined by a plurality of mutually connected, three dimensionally branched webs. The individual strands of polymeric material making up these branched webs are referred to herein as "struts."

Without being bound by theory, the cell size of the foam is believed to be important in determining the ability of the composition to hinder the digestion of sequestered materials. Small-celled foams are believed to sequester materials more effectively than large-celled foams, thereby inhibiting digestion by the gastric fluid.

In order to provide a high level of efficacy, it is desirable that the foams useful in the present invention have a high capacity to sequester or bind materials present in the gastrointestinal tract. For convenient dosage regimens, it is desirable that the effective dose occupies a relatively small volume on ingestion. It is thus desirable that the foams are highly compressible and sufficiently resilient to allow re-expansion of the foam in the gastrointestinal tract after long periods of storage in a highly compressed state. The more compressed the foam upon ingestion, the greater the subsequent volume expansion of that foam is in the gastrointestinal tract, and the greater the efficacy in terms of sequestering capacity for a given volume of ingested material. A high degree of compressibility allows a reduction in bulk and facilitates ingestion to provide convenient dosage regimens.

In order to provide a high capacity and a high degree of compressibility, the foam should have a relatively high void volume. A high void volume is characteristic of low-density foams. Foam density (i.e., in grams of foam per cubic centimeter of foam volume in air) is specified herein on a dry basis in the fully expanded state without any confining pressure. Any suitable gravimetric procedure that will provide a determination of mass of solid foam material per unit volume of foam structure can be used to measure foam density. For example, the ASTM gravimetric procedure described more fully in U.S. Pat. No. 5,387,207, Dyer et al., issued Feb. 7, 1995, is one method that can be employed for density determination.

The foams may comprise any of a variety of polymeric materials, provided such foams are non-digestible, non-absorbable, and open-celled, as described herein. Non-limiting examples of useful polymeric materials include celluloses, chitins, chitosans, natural sponges, synthetic sponges, polyvinyl acetate, polyvinyl alcohol, polyurethanes, polyacrylates, polymethacrylates, polystyrenics, polyolefins, copolymers thereof, mixtures thereof, and the like. Synthetic foams may be prepared by various techniques well known to those skilled in the art. Examples of such techniques include the use of blowing agents, porogens, thermally induced phase separation, non-solvent induced phase separation, dispersion techniques, emulsions, inverse emulsions, and the like.

HIPE Foams

Preferred polymeric foams useful herein are prepared by polymerization of the oil phase of certain water-in-oil emulsions having a relatively high ratio of water phase to oil phase, commonly known in the art as "HIPE." As used herein, a polymeric foam material which results from the polymerization of such emulsions is referred to herein as a "HIPE foam." HIPE foams comprise a generally lipophilic or amphiphilic, flexible or semi-flexible, nonionic polymeric foam structure of interconnected open-cells.

HIPE foams suitable for use in the present invention and processes suitable for preparing such foams are described in U.S. Pat. No. 5,149,720, DesMarais et al., issued Sep. 22, 1992, U.S. Pat. No. 5,260,345, DesMarais et al., issued Nov. 9, 1993; U.S. Pat. No. 5,268,224 DesMarais et al., issued Dec. 7, 1993; U.S. Pat. No. 5,563,179, Stone et al., issued Oct. 8, 1996; U.S. Pat. No. 5,650,222, DesMarais et al., issued Jul. 22, 1997; U.S. Pat. No. 5,741,518, DesMarais et al., issued Apr. 21, 1998; and U.S. Pat. No. 5,827,909, DesMarais et al., issued Oct. 27, 1998.

A. Components of the HIPE

HIPE foams may be prepared via polymerization of a HIPE comprising a discontinuous water phase and a continuous oil phase, wherein the ratio of water-to-oil is at least about 10:1, by weight. The water phase generally contains an electrolyte and a water-soluble initiator. The oil phase generally consists of substantially water-insoluble monomers which can be polymerized by free radicals, an emulsifier, and other optional ingredients defined below. The monomers are selected so as to confer the properties desired in the resulting polymeric foam, for example mechanical integrity sufficient for the end use, flexibility, resilience, lipophilic character, and economy. Preferably, the glass transition temperature (Tg) of the resulting foam will be from about −40° to about 90° C. so as to confer sufficient flexibility to allow for compression of the foam to reduce its bulk and thereby facilitate ingestion.

1. Oil Phase Components of the HIPE

The continuous oil phase of the HIPE comprises monomers that are polymerized to form the solid foam structure and the emulsifier necessary to stabilize the emulsion. In general, the monomers will include from about 20% to about 95%, alternatively from about 45% to about 65%, by weight of at least one substantially water-insoluble monofunctional monomer capable of forming an atactic amorphous polymer having a glass transition temperature (Tg) of about 90° C. or lower. This co-monomer is added to lower the overall Tg of the resulting HIPE foam. Exemplary monomers of this type include $C_4$-$C_{14}$ alkyl acrylates and $C_6$-$C_{16}$ methacrylates such as 2-ethylhexyl acrylate, isobornyl acrylate, n-butyl acrylate, hexyl acrylate, n-octyl acrylate, nonyl acrylate, decyl acrylate, isodecyl acrylate, tetradecyl acrylate, benzyl acrylate, nonyl phenyl acrylate, isobornyl methacrylate, hexyl methacrylate, octyl methacrylate, nonyl methacrylate, decyl methacrylate, isodecyl methacrylate, dodecyl methacrylate, and tetradecyl methacrylate; substituted acrylamides or methacrylamides, such as N-octadecyl (meth)acrylamide; dienes such as isoprene, butadiene, chloroprene, piperylene, 1,3,7-octatriene, beta-myrcene and amyl butadiene; substituted $C_4$-$C_{12}$ styrenics such as p-n-octyl styrene; vinyl norbornene; and combinations of such monomers.

The oil phase will also comprise from about 5% to about 80%, by weight, of a substantially water-insoluble, polyfunctional crosslinking agent. This co-monomer is added to confer strength to the resulting HIPE foam. Exemplary crosslinking monomers of this type encompass a wide variety of monomers containing two or more activated vinyl groups, such as the divinyl benzenes and analogs thereof. These analogs include m,p-divinyl benzene mixtures with ethyl styrene, divinyl naphthalene, trivinyl benzene, divinyl alkyl benzenes, divinyl biphenyls, divinyl phenyl ethers, divinyl ferrocenes, divinyl furans, and the like. Other useful crosslinking agents may be selected from a group derived from the reaction of acrylic acid or methacrylic acid with polyfunctional alcohols and amines. Non-limiting examples of this group include 1,6-hexanedioldiacrylate, 1,4-butanedioldimethacrylate, trimethylolpropane triacrylate, hexamethylene bisacrylamide, and the like. Other examples of crosslinking monomers include divinyl sulfide, divinyl sulfone, and trivinyl phosphine. Other crosslinkers useful in this regard are well known to those skilled in the art. It should be noted that the weight fraction of the crosslinking component is calculated on the basis of the pure crosslinker in cases wherein the crosslinking monomer is commonly used as a mixture (e.g., divinyl benzene often is a 55% pure mixture with the balance being ethyl styrene). Mixtures of the above crosslinkers may also be employed (e.g., divinyl benzene and 1,6-hexanedioldiacrylate).

Other substantially water-insoluble comonomers may be added to the oil phase in amounts of from 0% to about 70%, alternatively from about 15% to about 40%, by weight, to modify properties in other ways. In certain cases, "toughening" monomers may be desired which impart toughness to the resulting HIPE foam equivalent to that provided by styrene. These include styrenics, such as styrene, 4-tert-butyl styrene, and ethyl styrene, and methyl methacrylate. Also included are styrenics and other compounds which may also help reduce the Tg or enhance the strength of the resulting HIPE foam such as p-n-octyl styrene. Monomers may be added to form a wettable surface on the HIPE foam struts, or for any other purpose. Other additives, such as fillers, or other materials as may be desired, can also be added to the HIPE prior to curing.

Monomers that contain functional groups may also be employed. For example, monomers with amine groups may be useful in providing foam with enhanced ability to bind fatty acids. Dialkylaminoalkyl (meth)acrylates such as dimethylaminoethyl acrylate are non-limiting examples of such monomers. Because such functional groups are generally detrimental to emulsion formation and/or stability, monomers may be useful which facilitate the formation of functional groups via chemical modification of the foam after polymerization. For example, an oil phase comprising the tert-butyl or cyclohexyl ester of an acrylate, methacrylate, acrylamide, or methacrylamide may be used to make HIPE foam. After curing the foam, the tert-butyl or cyclohexyl ester groups may be hydrolyzed under appropriate conditions to yield foam containing the corresponding functional groups. Alternatively, monomers that contain functional groups, or those which facilitate the formation of functional groups may be polymerized or co-polymerized with other monomers prior to incorporation into the oil phase.

2. Emulsifier

An emulsifier is necessary for forming and stabilizing the HIPE. Suitable emulsifiers are advantageously added to the oil phase such that the oil phase comprises from about 1% to about 20% emulsifier, by weight of the oil phase. Emulsifiers that are particularly useful for stabilizing HIPE at high temperatures are preferred. The following discussion sets forth the particularly preferred, oxidatively stable emulsifier compositions.

2.1 Primary Emulsifier

The emulsifier component of the oil phase comprises at least a primary emulsifer. Suitable primary emulsifiers are well known to those skilled in the art. Particularly preferred emulsifiers include CRILL-6™, SPAN 20™, SPAN 40™, SPAN 60™, and SPAN 80™. These are nominally esters of sorbitan derived from lauric, myristic, stearic, and oleic acids, respectively. Other preferred emulsifiers include the diglycerol esters derived from monooleate, monomyristate, monopalmitate, and monoisostearate acids. Another preferred emulsifier is diglycerol monooleate (DGMO). Mixtures of these emulsifiers are also particularly useful, as are purified versions of each, specifically sorbitan esters containing minimal levels of isosorbide and polyol impurities.

A preferred emulsifier is described in U.S. Pat. No. 6,207,724, Hird et al., issued Mar. 27, 2001. Such emulsifiers comprise a composition made by reacting a hydrocarbyl substituted succinic acid or anhydride or a reactive equivalent thereof with either a polyol (or blend of polyols), a polyamine (or blend of polyamines) an alkanolamine (or blend of alkanol amines), or a blend of two or more polyols, polyamines and alkanolamines. The lack of substantial carbon-carbon unsaturation renders them substantially oxidatively stable.

2.2 Secondary Emulsifier

In addition to these primary emulsifiers, secondary emulsifiers can be optionally included in the emulsifier component. Again, those skilled in the art will recognize that any of a variety of known emulsifiers may be used. These secondary emulsifiers are at least cosoluble with the primary emulsifier in the oil phase. Secondary emulsifiers can be obtained commercially or prepared using methods known in the art. The preferred secondary emulsifiers are ditallow dimethyl ammonium methyl sulfate and ditallow dimethyl ammonium methyl chloride. Wherein these optional secondary emulsifiers are included in the emulsifier component, it is typically at a weight ratio of primary to secondary emulsifier of from about 50:1 to about 1:4, alternatively from about 30:1 to about 2:1.

As is indicated, those skilled in the art will recognize that any suitable emulsifier(s) can be used in the processes for making the foams useful in the present invention. See e.g., U.S. Pat. No. 5,387,207, Dyer et al., issued Feb. 7, 1995 and U.S. Pat. No. 5,563,179, Stone et al., issued Oct. 8, 1996.

The oil phase used to form the HIPE comprises from about 85% to about 98% monomer component and from about 2% to about 15% emulsifier component, all by weight of the oil phase. Preferably, the oil phase will comprise from about 90% to about 97% monomer component and from about 3% to about 10% emulsifier component, all by weight of the oil phase. The oil phase also can contain other optional components. One such optional component is an oil-soluble polymerization initiator of the general type well known to those skilled in the art, such as described in U.S. Pat. No. 5,290,820, Bass et al., issued Mar. 1, 1994.

3. Aqueous Phase Components

The discontinuous aqueous internal phase of the HIPE is generally an aqueous solution containing one or more dissolved components. One essential dissolved component of the aqueous phase is a water-soluble electrolyte. The dissolved electrolyte minimizes the tendency of monomers, co-monomers, and crosslinkers that are primarily oil soluble to also dissolve in the aqueous phase.

Any electrolyte capable of imparting ionic strength to the water phase can be used. Preferred electrolytes are mono-, di-, or trivalent inorganic salts, such as the water-soluble halides (e.g., chlorides), nitrates, and sulfates of alkali metals and alkaline earth metals. Non-limiting examples include sodium chloride, calcium chloride, sodium sulfate, and magnesium sulfate. For HIPE's that are used to make polymeric foams, calcium chloride is most preferred. Generally, the electrolyte will be utilized in the water phase of the HIPE in a concentration in the range of from about 0.2% to about 40%, alternatively from about 1% to about 20%, and alternatively from about 1% to about 10%, all by weight of the water phase.

Another component of the aqueous phase is a water-soluble free-radical initiator, as will be known to the art. The initiator can be present at up to about 20 mole percent based on the total moles of polymerizable monomers present in the oil phase. More preferably, the initiator is present in an amount of from about 0.001 to about 10 mole percent based on the total moles of polymerizable monomers in the oil phase. Suitable initiators include ammonium persulfate, sodium persulfate, and potassium persulfate.

B. Processing Conditions for Obtaining HIPE Foams

HIPE Foam preparation typically involves the steps of: 1) forming a stable high internal phase emulsion (HIPE); 2) curing this stable emulsion under conditions suitable for forming a cellular polymeric structure; 3) compressing and washing the cellular polymeric structure to remove the original residual aqueous phase from the polymeric foam structure and, if necessary, treating the polymeric foam structure with a hydrophilizing surfactant and/or hydratable salt to deposit any needed hydrophilizing surfactant/hydratable salt, and 4) thereafter dewatering this polymeric foam structure.

1. Formation of HIPE

The HIPE is formed by combining the aqueous and oil phase components in a ratio ranging from about 8:1 to about 140:1, alternatively from about 10:1 to about 75:1, alternatively from about 13:1 to about 65:1, by weight. As discussed above, the oil phase will typically contain the requisite monomers, co-monomers, crosslinkers, emulsifiers, and co-emulsifiers, as well as optional components as may be desired. The aqueous phase will typically contain electrolyte or electrolytes and polymerization initiator or initiators.

The HIPE can be formed from the combined oil and aqueous phases by subjecting these combined phases to shear agitation. Shear agitation is generally applied to the extent and for a time period necessary to form a stable emulsion. Such a process can be conducted in either in batches or in a continuous fashion and is generally carried out under conditions suitable for forming an emulsion where the aqueous phase droplets are dispersed to such an extent that the resulting polymeric foam will have the requisite structural characteristics. Emulsification of the oil and aqueous phase combination will frequently involve the use of a mixing or agitation device such as an impeller.

One preferred method of forming HIPE foam involves a continuous process that combines and emulsifies the requisite oil and aqueous phases. In such a process, a liquid stream comprising the oil phase is formed. Concurrently, a separate liquid stream comprising the aqueous phase is also formed. The two separate streams are provided to a suitable mixing chamber or zone at a suitable emulsification pressure and combined therein such that the desired ratio of aqueous phase to oil phase is achieved.

In the mixing chamber or zone, the combined streams are generally subjected to shear agitation provided, for example, by an impeller of suitable configuration and dimensions, or by any other means of imparting shear or turbulent mixing generally known to those skilled in the art. Shear will typically be applied to the combined oil/water phase stream at an appropriate rate and extent. Once formed, the stable liquid HIPE can then be withdrawn or pumped from the mixing chamber or zone. This preferred method for forming HIPE via a continuous process is described in detail in U.S. Pat. No. 5,149,720, DesMarais et al., issued Sep. 22, 1992. See also, U.S. Pat. No. 5,827,909, DesMarais, issued on Oct. 27, 1998, which describes an improved continuous process having a recirculation loop for the HIPE. The process also allows for the formation of two or more different kinds of HIPE in the same vessel as disclosed in U.S. Pat. No. 5,817,704, Shiveley et al., issued Oct. 6, 1998. In this example, two or more pairs of oil and water streams may be independently mixed and then blended as required. Alternatively, in-line mixing techniques may be used, such as those described in U.S. patent application Ser. No. 09/684,037, filed in the names of Catalfamo et al. on Oct. 6, 2000.

2. Polymerization/Curing of the HIPE Oil Phase

The HIPE formed will generally be collected in or poured into a suitable reaction vessel, container or region to be polymerized or cured. In one embodiment, the reaction vessel comprises a tub constructed of polyethylene from which the eventually polymerized/cured solid foam material can be easily removed for further processing after polymerization/curing has been carried out to the extent desired. It is usually preferred that the temperature at which the HIPE is poured into the vessel be approximately the same as the polymerization/curing temperature.

The emulsifiers of the present invention are also suitable for stabilizing the HIPE during relatively rapid curing at elevated temperatures. Suitable polymerization/curing conditions will vary, depending upon the monomer and other makeup of the oil and water phases of the emulsion (especially the emulsifier systems used), and the type and amounts of polymerization initiators used. Frequently, however, suitable polymerization/curing conditions will involve maintaining the HIPE at elevated temperatures above about 50° C., alternatively above about 65° C., and alternatively above about 80° C., for a time period ranging from about 20 seconds to about 64 hours, alternatively from about 1 minute to about 48 hours. Conditions which aid in reducing the curing time are discussed in detail in U.S. Pat. No. 5,189,070, Brownscombe et al., issued Feb. 23, 1993 and in U.S. patent application Ser. No. 09/255,225, filed in the name of DesMarais et al. on Feb. 22, 1999.

A porous water-filled open-celled HIPE foam is typically obtained after curing the HIPE. This cured HIPE foam may be cut or sliced into a sheet-like form. It has been found that such sheets of cured HIPE foam may be readily processed by subsequent treating/washing and dewatering steps useful for modifying foam properties for end use applications. The cured HIPE foam may be cut or sliced to provide a cut thickness in the range of from about 0.08 cm to about 2.5 cm. Alternatively, the foam may be milled, ground, or otherwise comminuted into particles of the desired size and shape.

3. Treating/Washing HIPE Foam

The solid polymerized HIPE foam formed will generally be filled with residual water phase material used to prepare the HIPE. This residual water phase material (generally an aqueous solution of electrolyte, residual emulsifier, and polymerization initiator) should be at least partially removed prior to further processing and use of the foam. Removal of this original water phase material will usually be carried out by compressing the foam structure to squeeze out residual liquid and/or by washing the foam structure with water or other aqueous washing solutions. Frequently several compressing and washing steps, for example, from 2 to 4 cycles, will be used.

After the original water phase material has been removed to the extent required, the HIPE foam, if desired, can be treated, for example, by continued washing, with an aqueous solution of a suitable hydrophilizing surfactant and/or hydratable salt.

Optionally, residual surfactant and any other extractable materials can be removed by washing with an appropriate solvent such as 2-propanol, ethanol, or acetone.

4. Foam Dewatering

After the HIPE foam has been treated/washed, it will generally be dewatered. Dewatering can be achieved by compressing the foam to squeeze out residual water or other solvent, by subjecting the foam and the liquid therein to temperatures of from about 60° C. to about 200° C., or to microwave treatment, by vacuum dewatering or by a combination of compression and thermal drying/microwave/vacuum dewatering techniques. The dewatering step will generally be carried out until the HIPE foam is ready for use and is as dry as practicable. One means of dewatering is described in U.S. patent application Ser. No. 09/687,280, filed in the names of Weber et al. on Oct. 13, 2000, which describes capillary methods of dewatering HIPE foams. Such capillary dewatering may optionally be followed by a drying step.

C. HIPE Foam Properties

In addition to being non-absorbable, non-digestible, open-celled foams, preferred HIPE foams useful in the present invention have certain desirable properties. Non-limiting examples of such properties are detailed below:

1. Microstructure

HIPE foam cells will frequently be substantially spherical in shape. The size or diameter of such spherical cells is a commonly used parameter for characterizing foams in general. Since cells in a given sample of polymeric foam will not necessarily be of approximately the same size, an average cell size, i.e., average cell diameter, will often be specified. A method for measuring cell size is disclosed in U.S. Pat. No. 5,563,179, Stone et al., issued Oct. 8, 1996.

The preferred HIPE foams useful in the present invention may have average cell diameters of less than about 150 μm, alternatively from about 5 μm to about 130 μm, alternatively from about 10 μm to about 50 μm, and alternatively from about 15 μm to about 35 μm.

2. Density

Preferred HIPE foams useful in the present invention have dry basis density values of less than about 0.1 g/cc, alternatively from about 0.01 g/cc to about 0.1 g/cc, alternatively from about 0.01 g/cc to about 0.05 g/cc, and alternatively from about 0.01 g/cc to about 0.03 g/cc.

3. Glass Transition Temperature (Tg)

An important factor in determining the compressibility of the foam is the flexibility of the polymer from which the foam is comprised. Flexibility is typically characteristic of polymers with relatively low glass transition temperatures. The glass transition temperature (Tg) represents the midpoint of the transition between the glassy and rubbery states of the polymer. Foams comprising one or more polymers with a Tg higher than the temperature of use can be very strong but will tend to be rigid and suffer from permanent damage to the foam structure when compressed to a high degree. Furthermore, foams comprising one or more high Tg polymers typically take a long time to recover to an expanded state after having been stored in a compressed state for prolonged periods. The desired combination of mechanical properties, specifically compressibility and resilience, will necessitate selection between a range of monomer types and levels to achieve the desired end properties.

The Tg of the foams is determined by Dynamic Mechanical Analysis (DMA) using the method described in U.S. Pat. No. 5,817,704, Shiveley et al., issued Mar. 8, 1996. The HIPE foams useful in the present invention will preferably have glass transition temperatures from about −40° C. to about 90° C. determined according to this method.

One of ordinary skill in the art will understand that the Tg may be affected by the presence of lipohilic materials which may serve to plasticize the polymer from which the foam is comprised. The measurement of Tg should take into account possible plasticaization under in-use conditions.

4. Resilience

The polymer from which the HIPE foam is comprised is preferably sufficiently resilient to allow re-expansion of the foam in the gastrointestinal tract after long periods of storage in a highly compressed state. Typically, this preferred resiliency requires that the polymer be crosslinked to prevent permanent deformation form occurring via stress-relaxation and/or creep. One measure of such permanent deformation is creep recovery. It should be noted that many synthetic polymers are thermoplastic and are thus susceptible to stress relaxation and creep. In such cases, creep recovery can be very slight. For example, a nonwoven polypropylene fiber web of 1 mm thickness loaded to a pressure of 5.1 kPa at 31° C. for 4 hours recovers only slightly after the weight is removed. On the other hand, because they are highly crosslinked, the preferred HIPE foams useful in the present invention provide excellent creep recovery. Suitably, a HIPE foam used in the present invention when similarly loaded to a pressure of 5.1 kPa at 31° C. will recover virtually all of its original thickness within a relatively short period, depending on the Tg of the polymer from which the HIPE foam is comprised.

5. Specific Surface Area

Another key parameter of the HIPE foams useful in the present invention is their specific surface area, which is determined by both the dimensions of the cellular units in the foam and by the density of the polymer, and is thus a way of quantifying the total amount of solid surface provided by the foam.

Specific surface area is determined by measuring the amount of capillary uptake of a low surface tension liquid (e.g., ethanol) which occurs within a foam sample of known mass and dimensions. A detailed description of such a procedure for determining foam specific surface area via the capillary suction method is set forth in the test methods section of in U.S. Pat. No. 5,563,179, Stone et al., issued Oct. 8, 1996. Other similar tests for determining specific surface area can be used with the present foams. Preferred HIPE foams according to the present invention have a specific surface area per unit volume that is greater than about 0.01 $m^2/cc$; alternatively greater than about 0.015 $m^2/cc$, and alternatively greater than about 0.02 $m^2/cc$.

6. Lipophilicity or Amphiphilicity of the Foam

The HIPE foams useful in the present invention will be generally lipophilic or amphiphilic to facilitate the sequestering of lipids or other lipophilic materials by the foam in the digestive tract. For example, the HIPE foam structures may be rendered both lipophilic and hydrophilic (i.e. amphiphilic) by the presence of surfactants and salts left in the foam structure after polymerization, or by treatment with suitable wetting agents. Alternatively, the surfactants and salts may be removed from the structure to render the HIPE foam lipophilic (but hydrophobic). Lipophilic or amphiphilic foams are useful for sequestering lipophilic substances present in the digestive tract and/or for stiffening such substances for mitigation of undesirable effects such as anal leakage. Amphiphilic HIPE foams may also be utilized for sequestering aqueous dietary liquids for mitigation of undesirable effects such as diarrhea.

When utilized, the open-celled foam is preferably included in a given compositions at a level that is safe and effective for the particular purpose and animal being treated. As an example, the compositions described herein may optionally comprise at least about 0.05%, at least about 0.1%, at least about 0.25%, at least about 0.4%, or at least about 0.5%, or at least about 2.5% of the open-celled foam, by weight of the composition. In other preferred compositions, the compositions may optionally comprise from about 0.05% to about 99%, from about 0.1% to about 95%, from about 0.25% to about 95%, from about 0.4% to about 95%, or from about 0.5% to about 95%, or from about 2.5% to about 95% of the stiffening agent, all by weight of the composition.

Methods of the Present Invention

The present methods are useful for a variety of purposes that are related to stiffening various materials including, preferably, lipophilic substances. In particular, one embodiment of the present invention relates to method of administering compositions that are suitable for administration to an animal for the purpose of stiffening one or more lipophilic substances present in the gastrointestinal tract of the animal.

The compositions are therefore suitable for the purpose of stiffening, or increasing the viscosity of, undigested lipids, undigested lipid-substitutes, toxins, and/or other materials present in the gastrointestinal tract, as well as lipase inhibitors which are administered for any of a variety of purposes including effecting weight loss and other like purposes. The methods are therefore useful for treating gastrointestinal distress, treating fecal urgency, treating obesity, treating hyperlipidemia, treating diarrhea, inhibiting anal leakage, reducing levels of toxic substances (in, for example, the gastrointestinal tract), reducing blood cholesterol levels, inducing satiety, effecting weight loss, effecting weight control, treating Type II Diabetes, delaying onset of Type II Diabetes, preventing Type II Diabetes, and combinations thereof in an animal, either alone or with another functional substance such as a lipase inhibitor.

In particular, the methods of the present invention comprise administration of a present composition to an animal (preferably a mammal, and most preferably a human). Although the compositions may be administered in a variety of manners that will be well-known to those of ordinary skill in the art, oral administration is preferred. Frequency of administration is not limited. However, the present compositions are typically administered on an infrequent or as-needed basis or may be administered in a more routine manner weekly, daily, or on a more or less frequent basis. For example, the composition may be administered with meals or between meals at least once daily, or alternatively at least two to three times daily.

As used herein, the term "administer" with regard to a particular composition means to provide the composition to an animal (including oneself) and/or to direct, instruct, or advise the use of the composition for any purpose (preferably, for a purpose described herein). Wherein the administration of one or more of the present compositions or kits is directed, instructed or advised, such direction may be that which instructs and/or informs the user that use of the composition may and/or will provide one or more of the benefits described herein. Non-limiting examples of such instruction or information are set forth herein as part of the description of the present kits.

Administration which is directed may comprise, for example, oral direction (e.g., through oral instruction from, for example, a physician, health professional, sales professional or organization, and/or radio or television media (i.e., advertisement) or written direction (e.g., through written direction from, for example, a physician or other health professional (e.g., scripts), sales professional or organization (e.g., through, for example, marketing brochures, pamphlets, or other instructive paraphernalia), written media (e.g., internet, electronic mail, or other computer-related media), and/or packaging associated with the composition (e.g., a label present on a package containing the composition). As used herein, "written" includes through words, pictures, symbols, and/or other visible descriptors. Such direction need not utilize the actual words used herein, but rather use of words, pictures, symbols, and the like conveying the same or similar meaning are contemplated within the scope of this invention.

The present compositions, and the various components within the compositions, may be administered in accordance with various levels as one of ordinary skill in the art will understand. Additionally, preferred levels of the various components have been described herein above. Additionally or alternatively, as an example, the methods comprise administration to an animal of from about 2 mg to about 30 mg of stiffening agent, per kilogram of the animal, per dose (for example, up to three times daily). Additionally or alternatively, also as an example, for a human consuming a diet of approximately 600 grams of food per day (on a dry basis), a useful dose of stiffening agent may be may optionally be administered in ranges from about 0.01 grams to about 10 grams daily, or from about 0.1 grams to about 5 grams daily, or from about 0.5 grams to about 3 grams daily. Also as an example, the methods comprise administration to an animal of from about 1 mg to about 4 mg of lipase, per kilogram of the animal, per dose (for example, up to three times daily). Alternatively or additionally, wherein a lipase inhibitor is utilized, 0.002 grams to about 2 grams daily, or from about 0.01 grams to about 0.8 grams daily, or from about 0.06 gram about 0.4 grams daily may be administered. Where doses of a given composition are administered more than once daily, or less frequently, the ordinarily skilled artisan will be able to determine an appropriate dose.

Wherein the optional open-celled foam is used as described herein above, any safe and effective amount may be used, but very low doses may not be sufficiently efficacious and high dosages may be inconveniently large to administer. Dosage regimens include those where the diet of the animal comprises from about 0.02% to about 2%, alternatively from about 0.03% to about 1%, and alternatively from about 0.1% to about 0.5% of the foam, by weight of the diet on a dry basis. As an example, for a human consuming a diet of approximately 600 grams of food per day (on a dry basis), a useful dose would comprise from about 0.12 grams to about 12 grams; alternatively from about 0.18 grams to about 6 grams; and alternatively from about 0.6 to about 3 grams of foam per day. In the alternative, the dosage may be calculated as a percentage of ingested lipid. Useful dosage regimens include those where the foam is administered on a weight basis relative to ingested lipid, for example administering the foam in an amount which is from about 0.15% to about 15%, alternatively from about 0.2% to about 7%, and alternatively from about 0.75% to about 3.75% of the ingested lipid, all on a weight basis. As an example, for a human consuming a diet comprising about 80 grams of lipid per day, a useful dose would comprise from about 0.12 grams to about 12 grams, alternatively from about 0.16 grams to about 5.6 grams, and alternatively from about 0.6 grams to about 3 grams of foam per day.

It is understood that these dosage ranges are by way of example only, and that daily administration can be adjusted depending on various factors. The specific dosage of the component to be administered, as well as the duration of treatment, are interdependent. The dosage and treatment regimen will also depend upon such factors as the specific compound used, the treatment indication, the efficacy of the compound, the personal attributes of the animal (such as, for example, weight, age, gender and medical condition of the animal), compliance with the treatment regimen, and the presence and severity of any side effects of the treatment.

EXAMPLES OF THE PRESENT INVENTION

The following are examples of the present compositions, kits, and methods. The compositions are prepared utilizing conventional processes or, preferably, the processes described herein. The examples are provided to illustrate the invention and are not intended to limit the scope thereof in any manner.

Example 1

Groups of male, Sprague-Dawley rats (commercially available from Harlan Labs, Indianapolis, Ind.), were presented with a composition, which was a food composition, containing either 0.04% orlistat, by weight of the composition, or the combination of 0.04% orlistat and 1%, 0.5%, or 0.25% calcium stearate, all by weight of the composition. The fat content of each composition provided 30% of the consumed energy of the rat. Another group of rats (also male, Sprague Dawley, commercially available from Harlan Labs, Indianapolis, Ind.) were presented with the same food compositions, except devoid of orlistat and calcium stearate ("control compositions"). All rats consumed their respective compositions ad libitum for 11 days.

On the seventh and eleventh days of these dietary regimens, the appearance of each rat was viewed by assessors not aware of the identity of composition consumed by the rats. Separation of oil from the other fecal matter of each rat was determined by the use of a scale that quantified the fraction of the rat's fur that was coated with excreted dietary oil. A score of "5" indicated that approximately greater than 90% of the rat's fur showed evidence of oil. A score of "1" indicated that no oil was visible on the rat's fur. Intermediate scores of "2," "3," and "4" indicated partial covering of the rat's fur, with "2" corresponding to approximately 10% coverage or less, "3" corresponding to approximately greater than 10% to approximately 50% coverage, and "4" corresponding to approximately greater than 50% to approximately 90% coverage.

Assessments demonstrated that those rats that consumed the control composition were judged to have a mean fur appearance score of "1." Those rats which received the composition containing both orlistat and calcium stearate were judged to have mean fur appearance scores of "1.1," "1.2," and "1.4," for calcium stearate levels of 1%, 0.5%, and 0.25%, respectively. Those rats which received the composition containing orlistat, but no calcium stearate, were judged to have mean fur appeance scores of "2.4."

Example 2

Orlistat (60 mg) is deposited onto fumed silica (10 mg) from an alcohol solution (following evaporation of the solvent. The deposited orlistat is admixed with behenic acid (300 mg) and filled into a size 00 standard hard gelatin capsule. The capsule is administered to a human subject on a calorically restricted diet three times per day with each meal.

Example 3

An aqueous suspension containing ethyl behenate (10%, by weight of the suspension), orlistat (1.2%, by weight of the suspension), xanthan gum (0.2%, by weight of the suspension), sodium saccharin (0.2%, by weight of the suspension), and vanilla flavor (0.3%, by weight of the suspension) is prepared by adding melted ethyl behenate to xanthan gum under high shear conditions, followed by the cooled addition of orlistat, sodium saccharin, and flavor, also under high shear conditions. Five milliliters of the resulting suspension is administered orally to a human subject prior to each meal.

Example 4

XENICAL® is prescribed to an overweight human subject at a therapeutic dose of 120 mg orlistat taken with each of three daily meals. This dose causes a reduction in the absorption of dietary fat such that total caloric intake by the subject is reduced by approximately 10%, relative to the subjects normal dietary energy intake. Since this regimen of XENICAL® frequently results in anal leakage of unabsorbed fat, a separate regimen of magnesium stearate is provided to the subject. In particular, magnesium stearate is provided at an amount of 1 gram incorporated into a wafer that is consumed with each meal, resulting in a total consumption of 3 grams per day of magnesium stearate. The inclusion of magnesium stearate prevents the gastrointestinal discomfort and anal leakage of unabsorbed oil. The efficacy of the XENICAL® is unaffected by the addition of magnesium stearate to the diet.

Example 5

An overweight human subject is given a therapeutic dose of XENICAL@ (360 mg orlistat per day/three doses of 120 mg orlistat with each meal) to assist in the reduction of body weight. This dose results in preventing the absorption of 25% of the subject's normal consumption of dietary fat. As a result of this decreased absorption, unabsorbed fat separates from other fecal matter, resulting in gastrointestinal discomfort and uncontrolled seepage of oil from the anal sphincter.

When these symptoms are first observed, the regimen is modified to a combination of XENICAL® and behenic acid. At each meal, the subject consumes two capsules. The first capsule is XENICAL® (120 mg orlistat) while the second capsule contains the behenic acid (1.2 g). These capsules are co-packaged in a kit for the convenience of the subject.

Upon modification of the regimen, the excretion of dietary fat continues at a level of approximately 25% of the subject's normal consumption of dietary fat. However, the excreted fat is stiffened by the presence of behenic acid, thereby enabling the excretion of the fat without separation from other fecal matter.

Excreted fat accounts for a reduction in caloric intake of 225 kcal/day, equal to a reduction of total caloric intake by approximately 10%. Given this reduction, total body fat and weight decreases by approximately 0.5 kilograms every 12 days of the regimen.

What is claimed is:

1. A composition comprising:
    (a) a stiffening agent having a complete melting point of about 33° C. or greater which is selected from the group consisting of R—COOR', R—OR', R—CONR'R", R—NR'R", salts thereof, and mixtures thereof, wherein:
        (i) R is selected from the group consisting of alkyl radicals having from about 14 to about 24 carbon atoms, alkenyl radicals having from about 14 to about 24 carbon atoms, alkynyl radicals having from about 14 to about 24 carbon atoms, heteroalkyl radicals having from about 14 to about 24 carbon atoms, heteroalkenyl radicals having from about 14 to about 24 carbon atoms, and heteroalkynyl radicals having from about 14 to about 24 carbon atoms; and
        (ii) R' and R" are each, independently, selected from the group consisting of hydrogen, alkyl radicals, alkenyl radicals, alkynyl radicals, heteroalkyl radicals, heteroalkenyl radicals, and heteroalkynyl radicals; and
    (b) a lipase inhibitor; and
    (c) a non-digestible, non-absorbable, open-celled high internal phase emulsion (HIPE) foam.

2. The composition according to claim 1, wherein the stiffening agent is selected from the group consisting of fatty acids, salts of fatty acids, and mixtures thereof.

3. The composition according to claim 2 wherein the lipase inhibitor is selected from the group consisting of 2-amino-4H-3,1-benzoxazin-4-ones; 2-oxy-4H-3,1-benzoxazin-4-ones; 2-thio-4H-3,1-benzoxazin-4-ones; tetrahydrolipstatins; chiral alkylphosphonates; chiral isomers of beta-lactone; and mixtures thereof.

4. The composition according to claim 3 wherein the lipase inhibitor is a compound selected from the group consisting of tetrahydrolipstatin, lipstatin, and mixtures thereof.

5. The composition according to claim 4 comprising about 0.001% to about 15% of the lipase inhibitor and about 0.1% to about 99% of the stiffening agent, all by weight of the composition.

6. The composition according to claim 2 comprising about 0.2% to about 95% of the stiffening agent, by weight of the composition.

7. The composition according to claim 6 comprising about 0.8% to about 95% of the stiffening agent, by weight of the composition.

8. The composition according to claim 7 wherein the lipase inhibitor is tetrahydrolipstatin.

9. The composition according to claim 7 wherein the stiffening agent is selected from the group consisting of calcium stearate, behenic acid, and mixtures thereof.

* * * * *